US012688912B2

(12) United States Patent
Bhatt et al.

(10) Patent No.: US 12,688,912 B2
(45) Date of Patent: Jul. 21, 2026

(54) ARTIFICIAL INTELLIGENCE PREDICTIVE INTERACTIVITY BASED ON RECURSIVE DATA ANALYSIS

(71) Applicant: Myriad Genetics, Inc., Salt Lake City, UT (US)

(72) Inventors: Darshan Bhatt, Salt Lake City, UT (US); Tanya Imani-Farley, Salt Lake City, UT (US); Diego Vargas, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 119 days.

(21) Appl. No.: 18/690,243

(22) PCT Filed: Sep. 12, 2022

(86) PCT No.: PCT/US2022/043213
§ 371 (c)(1),
(2) Date: Mar. 7, 2024

(87) PCT Pub. No.: WO2023/043695
PCT Pub. Date: Mar. 23, 2023

(65) Prior Publication Data
US 2024/0371481 A1      Nov. 7, 2024

Related U.S. Application Data

(60) Provisional application No. 63/243,982, filed on Sep. 14, 2021.

(51) Int. Cl.
*G16H 10/60*      (2018.01)
*G06N 20/00*      (2019.01)
*G16H 20/30*      (2018.01)

(52) U.S. Cl.
CPC ............. *G16H 10/60* (2018.01); *G06N 20/00* (2019.01); *G16H 20/30* (2018.01)

(58) Field of Classification Search
CPC ......... G16H 10/60; G16H 20/30; G06N 20/00
See application file for complete search history.

(56) References Cited

U.S. PATENT DOCUMENTS 12,248,826 B2 *   3/2025  Gnanasambandam   .....................
                                                        G16H 20/60

FOREIGN PATENT DOCUMENTS

| WO | WO-2020/234388 A1 | 11/2020 |
| WO | WO-2021/014405 A1 | 1/2021 |
| WO | WO-2021/087370 A1 | 5/2021 |

OTHER PUBLICATIONS

Ko, Elsevier, 2010, pp. 541-554.*

(Continued)

*Primary Examiner* — Michael I Ezewoko
(74) *Attorney, Agent, or Firm* — Foley & Lardner LLP

(57) ABSTRACT

An artificial intelligence (AI) agent interacts with patients via a user interface presented on a computing device. The AI agent may be trained by generating, based on session logs of a cohort of subjects interacting with the user interface, one or more training datasets comprising data on user interactions with the user interface by subjects in the cohort, and data based on health records of the subjects in the cohort of subjects. Machine-learning techniques may be applied to the training datasets to train the AI agent. Based on interactions of a patient with the AI agent, the AI agent may generate a recommendation for a medical screening, a medical procedure, etc. The recommendation may additionally be based on data in an electronic health record of the patient. Data on interactions with additional patients may be used to update models employed through the AI agent.

20 Claims, 11 Drawing Sheets

(56) References Cited

OTHER PUBLICATIONS

Elalfy,Elsevier,2018,pp. 21-31,2018.*

International Search Report and Written Opinion on PCT/US2022/043213 Dtd Jan. 10, 2023, 8 pages.

* cited by examiner

200

201    Begin Creation

202    Admin Creates Components

204    Admin Creates Nodes

206    Admin Creates Flows

208    Admin Creates Assessment Using Nodes and Flows

210    Assessment Created

111

700

702 Welcome

704 Patient Demographics

706 Ancestry Select

710 Qualifying Question

714 Cancer History

712 Redirect to Learn More

716 Criteria Check

718 Redirect to MyWay

720 Patient Deomographics

722 Results

724 Redirect to Access

TRAINING
DATA
810

INITIAL MODEL
FORM
815

TRAINING
ENGINE
820

801

RESULTS
DATA
831

TRAINED
MODEL
830

NEW DATA
860

INFERENCE
ENGINE
850

RECOMMENDATIONS
855

802

116

| I/O Controller 1114 | Display Adapter 1112 | Monitor 1110 |

| Memory 1122 | Serial Port 1116 |

| Processor(s) 1120 | Keyboard 1106 |

| Printer 1104 | Fixed Disk 1108 |

1102

| External Interface 1118 |

1100

ARTIFICIAL INTELLIGENCE PREDICTIVE INTERACTIVITY BASED ON RECURSIVE DATA ANALYSIS

CROSS-REFERENCE TO RELATED APPLICATIONS

This application claims priority to and the benefit of U.S. Provisional Patent Application No. 63/243,982 filed Sep. 14, 2021, the entirety of which is herein incorporated by reference.

BACKGROUND

Collecting and analyzing patient data is a key part of offering personalized medical advice and recommendations. For example, asking about a patient's known allergies, family history, and physiological characteristics helps physicians and clinicians use reasoned analysis to arrive at diagnostic and therapeutic conclusions when presented with an opportunity to assist a patient. With the advent of modern computing technology, the reasoned analysis used by physicians and clinicians can be assisted through empirical data collection and analysis along with collected research data in communities at large. Further, the collected data, often referred to as assessment data, can be stored with a patient's electronic medical record (EMR) such that future analyses, diagnostics, and therapeutics may be recommended based, in part, on the historical collected assessment data.

In conventional data collection and assessment methods, information about a patient is gathered in a serial manner using a simple questionnaire. This is often accomplished by way of a physical sheet of paper, interview-styled interaction with a health care worker, or through a series of questions presented in an electronic format. However, such serially presented questions often do not allow for or otherwise imply that a question may be able to be answered more than once with differing information. That is, as a patient provides answers to questions in whatever format presented, there is no path to allow for answering of questions more than once with additional information. Further, without a way to loop back to questions, there can certainly be no path to influence the questions based on the answers or influence the manner in which questions are asked. Thus, conventional systems and methods that present a rigid and serial manner of assessment data collection lack in flexibility and intuitiveness. These drawbacks lead to health care recommendations that are not dynamic enough to provide the high level of reasoned analysis that modern computing technology is capable of providing.

SUMMARY

According to various aspects, potential embodiments of the present disclosure relate to a method comprising: providing an artificial intelligence (AI) agent to a patient to assess the patient via a user interface presented on a computing device, wherein the AI agent was trained by: generating, based on session logs of a cohort of subjects interacting with the user interface, one or more training datasets comprising (i) data on user interactions with the user interface by subjects in the cohort, and (ii) data based on health records of the subjects in the cohort of subjects; and applying one or more machine-learning techniques to the one or more training datasets to train the AI agent; generating, based on interactions of the patient with the AI agent and on data in an electronic health record of the patient, a recommendation for at least one of a medical screening or a medical procedure; and presenting the recommendation to at least one of the patient or a healthcare provider of the patient.

In various potential embodiments, the method comprises administering the recommended medical screening or the recommended medical procedure to the patient.

In various potential embodiments, the method comprises updating the AI agent based on the interactions of the patient with the AI agent.

In various potential embodiments, updating the AI agent comprises generating one or more updated training datasets and applying one or more machine-learning techniques to the updated training datasets.

In various potential embodiments, applying one or more machine-learning techniques to the one or more training datasets comprises applying a pattern recognition model or a classification model to recognize normal or abnormal patterns of interaction with the user interface.

In various potential embodiments, applying the one or more machine-learning techniques to the one or more training datasets comprises applying a regression model to identify causal factors for one or more medical screenings or procedures based on interactions of the subjects with the user interface.

In various potential embodiments, applying the one or more machine-learning techniques to the one or more training datasets comprises applying a decisioning model to identify interactions suited to obtaining certain information on subjects through the user interface.

In various potential embodiments, applying the one or more machine-learning techniques to the one or more training datasets comprises applying natural language processing (NLP) to responses by the subjects in the cohort.

In various potential embodiments, the user interface digitally presents a plurality of assessment questions to the patient using an interactive display on a computing device, wherein at least one assessment question comprises an assessment question suited to having multiple simultaneous answers.

In various potential embodiments, the AI agent, in response to receiving one answer to an assessment question suited to having multiple simultaneous answers, updates assessment data about the patient in an assessment database and recursively presents the assessment question suited to having multiple simultaneous answers to the patient again.

In various potential embodiments, the AI agent iteratively analyzes answers stored in the assessment database after each update to determine whether the stored answers indicate that the recommendation should be triggered.

In various potential embodiments, presenting the recommendation comprises electronically communicating assessment data and the recommendation to the healthcare provider.

In various potential embodiments, the data on user interactions indicates selections made through the user interface.

In various potential embodiments, the data on user interactions includes text entries submitted through the user interface.

In various potential embodiments, the data based on health records identifies at least one of medical screenings administered to the subjects in the cohort, medical procedures administered to subjects the subjects in the cohort, or medical conditions of the subjects in the cohort.

In various potential embodiments, the method comprises training the AI agent by applying the one or more machine-learning techniques.

According to various other aspects, potential embodiments of the present disclosure relate to a computing system comprising one or more processors configured to provide an artificial intelligence (AI) agent to a patient to assess the patient via a user interface presented on a computing device, wherein the AI agent was trained by: generating, based on session logs of a cohort of subjects interacting with the user interface, one or more training datasets comprising (i) data on user interactions with the user interface by subjects in the cohort, and (ii) data based on health records of the subjects in the cohort of subjects; and applying one or more machine-learning techniques to the one or more training datasets to train the AI agent; generate, based on interactions of the patient with the AI agent and on data in an electronic health record of the patient, a recommendation for at least one of a medical screening or a medical procedure; and present the recommendation to at least one of the patient or a healthcare provider of the patient.

In various potential embodiments, applying one or more machine-learning techniques to the one or more training datasets comprises at least one of applying: a pattern recognition model or a classification model to recognize normal or abnormal patterns of interaction with the user interface; a regression model to identify causal factors for one or more medical screenings or procedures based on interactions of the subjects with the user interface; a decisioning model to identify interactions suited to obtaining certain information on subjects through the user interface; or natural language processing (NLP) to responses submitted by the subjects in the cohort.

In various potential embodiments, the user interface digitally presents a plurality of assessment questions to the patient using an interactive display on the computing device, wherein at least one assessment question comprises an assessment question suited to having multiple simultaneous answers.

In various potential embodiments, the AI agent, in response to receiving one answer to an assessment question suited to having multiple simultaneous answers, updates assessment data about the patient in an assessment database and recursively presents the assessment question suited to having multiple simultaneous answers to the patient again; and In various potential embodiments, the AI agent iteratively analyzes answers stored in the assessment database after each update to determine whether the stored answers indicate that the recommendation should be triggered.

In various potential embodiments, the data on user interactions includes selections made through the user interface and text entries submitted through the user interface.

In various potential embodiments, the data based on health records identifies at least one of medical screenings administered to the subjects in the cohort, medical procedures administered to the subjects in the cohort, or medical conditions of the subjects in the cohort.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the invention can be combined with other aspects. Aspects can be implemented in any convenient form. For example, by appropriate computer programs, which may be carried on appropriate carrier media (computer readable media), which may be tangible carrier media (e.g. disks) or intangible carrier media (e.g. communications signals). Aspects may also be implemented using suitable apparatus, which may take the form of programmable computers running computer programs arranged to implement the aspect. As used in the specification and in the claims, the singular form of "a," "an," and "the" include plural referents unless the context clearly dictates otherwise.

BRIEF DESCRIPTION OF THE DRAWINGS

The subject matter presented herein will now be described, by way of example, with reference to the accompanying drawings, in which.

The accompanying drawings are not intended to be drawn to scale. Like reference numbers and designations in the various drawings indicate like elements. For purposes of clarity, not every component may be labeled in every drawing.

DETAILED DESCRIPTION

Figure 1:
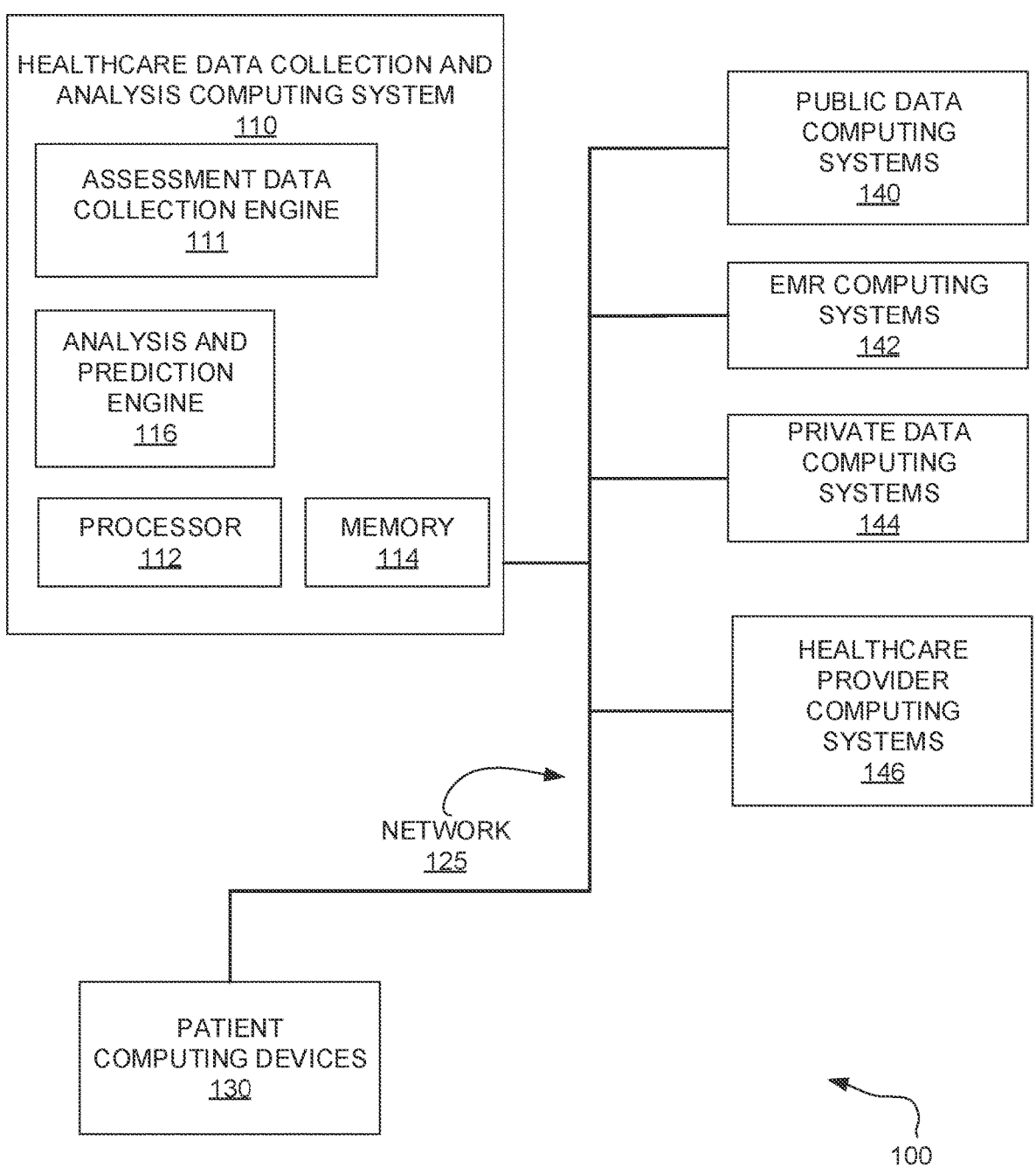
FIG. 1 is a block diagram of a computing environment for realizing the systems and methods for predictive health care recommendations based on recursive data collection according to an embodiment of the subject matter disclosed herein.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" as required by 35 U.S.C. § 112.

By way of an overview, the systems and methods described herein relate to obtaining needed healthcare data about a patient to inform and enhance health care decisions by and for patients. In various potential embodiments, an AI agent learns from (trains on) data on previous patients (e.g., subjects in a cohort of subjects). For example, the AI agent learns from past interactions of subjects with a user interface through which, for example, the subjects make selections and provide responses based on certain queries. The past interactions may indicate, for example, a patient with certain responses, selections, submissions, or other behaviors while engaging with the user interface has additional information relevant information not already provided, in response to which the user interface may adapt and engage with the patient to obtain the additional information from the patient. Similarly, when viewed in light of information in electronic health records of the subjects, the past interactions may indicate that certain other data information should be requested to get a better understanding of the patient's health and medical needs. The AI agent is better able to engage patient In one embodiment, a computer-based method comprises digitally presenting a plurality of assessment questions (e.g., questions about the patient's health, person, history, and past diagnostics and/or therapeutics) to a patient using an interactive display on a computing device. The assessment questions may be presented via an AI agent. In this presentation of questions, at least one assessment question is suited to having multiple simultaneous answers. For example, the patient may have multiple simultaneous answers to family history of cancer diagnoses. Thus, this question may be presented several times in a recursive and iterative manner. As the patient answers questions, each answer may be iteratively stored in a memory and/or database and the collection of answers in the memory and/or database may be analyzed after each update to determine is the collective stored answers indicate that a recommendation should be triggered. For example, if enough data is collected about multiple instances of a family history with a specific cancer, then the specific cancer test may be recommended. As the data is collected, numerous follow-on actions may result using the system, such as integration with a global database of records, communication of the assessment data to the patient or a third-party physician, and altering of the algorithm for the analysis using a machine learning feedback loop.

The above summarized system and methods may have several benefits in the practice of medicine. A first benefit, this novel method improves patient care and addresses common pain points in genetic screening and testing such as cumbersome and duplicative assessment surveys. In a follow-on benefit, iteratively and recursively presenting assessment question results in simplifying the process of gathering a patient's personal and family history of cancer, relevant order information and demographics. Further, the iterative and recursive questions that are part of an assessment are configurable based on previously assembled results as well as developer-based and provider-based feedback This results in accurate patient identification based on guidelines from national societies (NCCN, USPSTF, ASBS) as well as proprietary identification strategy. Further, results and recommendations can be sent instantly and securely to third-party provider portals or EMR systems (used interchangeably with Electronic Health Record (EHR) systems) whereupon test order forms may already be pre-populated with relevant data from the collected assessment data.

There are also further benefits to third-party healthcare providers such as saving clinic time by collecting important information quickly and easily thereby allowing assessing of patients in a timely manner. The global nature of the assessment data collection also generates confidence that patients are being evaluated through a reliable service. Such benefits elevate the patient experience by increasing education and awareness to specific aspects of healthcare such as hereditary cancer. Lastly, the systems and methods described herein assists with removing human error typically caused by manual entry of data and reduces missing information through auto-filling of electronic test request for quick ordering. These and other aspects may be more readily understood and further detailed with respect to the detailed description below with reference to FIGS. 1-11.

Turning attention to the figures, FIG. 1 is a block diagram of a computing environment for realizing the systems and methods for predictive health care recommendations based on recursive data collection according to an embodiment of the subject matter disclosed herein. The overall computing environment 100 may be generally comprised of several sets of computing devices that are all communicatively coupled to each other through a computing network 125, such as the Internet, though the network 125 may be a local Intranet or a virtual private network or the like. These generalized categories of the coupled computing devices and/or systems include a healthcare data collection and analysis server computer 110, one or more patient computing-devices 130, and one or more data-service computing devices, such as public data collection systems 140, private data collection systems 144, Electronic Medical Record (EMR)/Electronic Health Record (EHR) systems 142, and healthcare provider computing systems 146. Other data-collection and/or data provision services (such as government information service computing systems, research institution computing systems, and the like) are contemplated but not shown in this figure here for brevity. Collectively, these computing devices may be used to receive and send data patient data, assessment data, diagnostic data, and/or therapeutics data. The healthcare data collection and analysis server computer 110, includes one or more local processors 112 that utilizes one or more memories 114 in conjunction with a healthcare data analysis and prediction engine 116 and a health care assessment data collection engine 111.

In known conventional systems, many healthcare data collection and analysis tools are simply maps with data where users can answer unchanging questions in a serial manner to arrive at a recommendation, diagnostic or other therapeutic suggestion. But these conventional tools do not offer recursive data collection, assimilation, or analysis that would transform the originally presented questions into a responsive interactive collection of initial data that, in turn, informs a more useful predictive function. That is, conventionally speaking, no recursively gleaned conclusions are generated, and no predictive vectors are generated in response to such dynamic collection of data at the initial stages. For example, an assessed recommendation that patients that enter assessment data about family cancer history often stop at one entry for one family member with a history of cancer may not trigger the assessment recommendation based upon one family member having a history of cancer. Without a recursive and dynamically interactive assessment, this key data may go uncollected and result in the lack of a proper assessment. Utilizing the overall system 100 of FIG. 1, one may take advantage of all recursively and dynamically collected data using the health care assessment data collection engine 111 to glean the proper data entries during the assessment phase. This, in turn, will inform healthcare data analysis and prediction engine 116 with more accurate patient data from recursive assessments leading to greater accuracy and predictability for further testing, diagnostics, and therapeutics. This may be accomplished by training a prediction engine through iterative data assimilation in an algorithmic method as discussed further below with respect to FIG. 8. Further, providers and patients may also utilize the modelling and prediction engine 116 to interpret answers to questions posed through interactive (e.g., recursive and dynamic) questionnaires to parse differing assessment data points into meaningful matches of available health care decisions. This may be accomplished by utilizing a trained prediction engine through iterative data collection to produce a more suitable set of health care recommendations in an algorithmic method as discussed further below with respect to FIG. 9. Prior to discussing the specific algorithmic methods for machine learning that can be realized using the healthcare data collection and analysis system 100 of FIG. 1, a more in-depth description of the computer blocks, functionality and components of the assessment data collection system is presented with respect to FIGS. 2-7.

Figure 2:
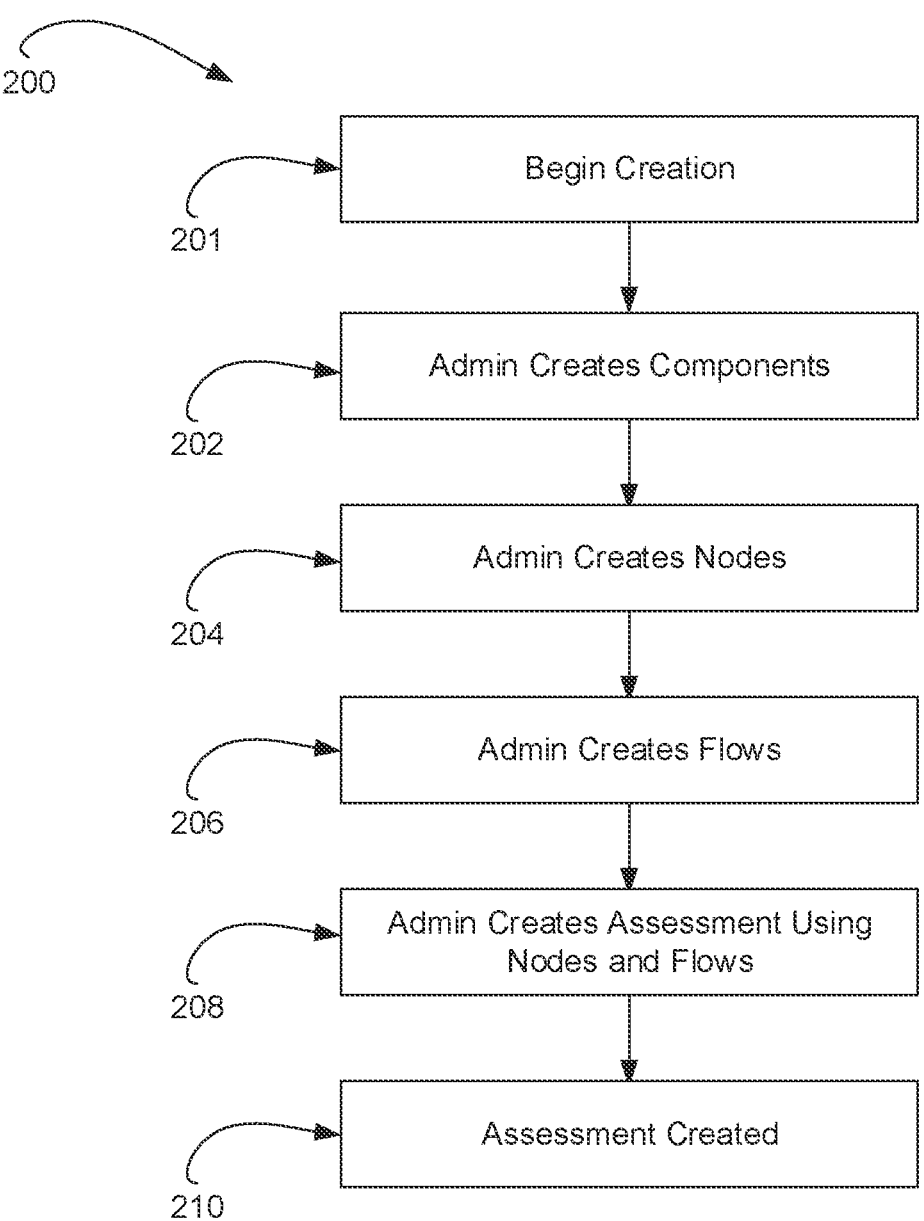
FIG. 2 is a flow diagram of computer-based method of establishing an assessment to be used within the system and method of FIG. 1 according to an embodiment of the subject matter disclosed herein.

FIG. 2 is a flow diagram of computer-based method 200 for establishing an assessment to be used within the healthcare data collection and analysis prediction engine 116 of FIG. 1 according to an embodiment of the subject matter disclosed herein. To properly utilize the capabilities of the healthcare data collection and analysis prediction engine

116, a coordinator designs an assessment (for use within health care assessment data collection engine 111) that aims to collect enough data points about a patient so as to be as accurate and complete as possible. Designing an assessment will involve configuring an interactive and recursive user-facing (e.g., patient-facing) questionnaire that steps through specific questions to elicit multiple choice answers or narrative answers. Thus, a coordinator may design several different assessments based on the recommendations sought. For example, one assessment may be designed to assess risk of colon cancer, while another assessment may be designed to assess risk of breast cancer. In other examples, assessments may be designed to assess reproductive health factors. Still other assessments may be directed to general health overall. Any assessment with any design of interactive and recursive questions may be designed according to a coordinator's desired focus.

The assessment creation method may begin at step 201. Alternatively, this step may also begin with a desire to alter an existing assessment. As a creator has a plan for a specific focus of the assessment, the creator will determine specific components of various decision points for a suitable recommendation for the specific assessment. That is, any decision about recommending an action will be based on a number of factors (e.g., components) and the creator assembles all components of a specific assessment at step 202. Once all components are established for a new (or altered) assessment, the creator may then group the component into nodes. For example, there may be several components regarding family history with respect to cancer, e.g., father's history, mother's history, generational history, and the like. Thus, all questions about a patient's history with cancer may be grouped into a single node. The establishment of nodes occurs at step 204.

Once nodes are created, the creator may then arrange each node into a specific workflow between nodes at step 206. That is, the arrangement of the nodes as well as the arrangement of components within each node may be laid out in a specific order, called a workflow. In this manner, the creator may choose to have a serial flow of nodes, or more likely and one of the focuses of this disclosure is to have recursive flows, e.g., loopbacks to the same node in an effort to provide additional differential answers to questions about specific components in the assessment. Workflows may also exhibit loop forward paths as well such as when a patient may answer a threshold question within a node the nullifies further answers associated with additional components within the node. Thus, some questions may be skipped (e.g., feed-forward) in an effort to streamline the assessment. Taken together, all components, nodes, and flows are assembled into an assessment ready-for-use assessment within the health care assessment data collection engine 111 at step 208. At step the 210, the assessment is created and published to the health care assessment data collection engine 111. FIGS. 4-7, as discussed below, provide several examples of created workflows for use within the health care assessment data collection engine 111, but prior to that, methods for collection of assessment data and analysis of the collected data to arrive at one or more actions is presented next with respect to FIG. 3.

Figure 3:
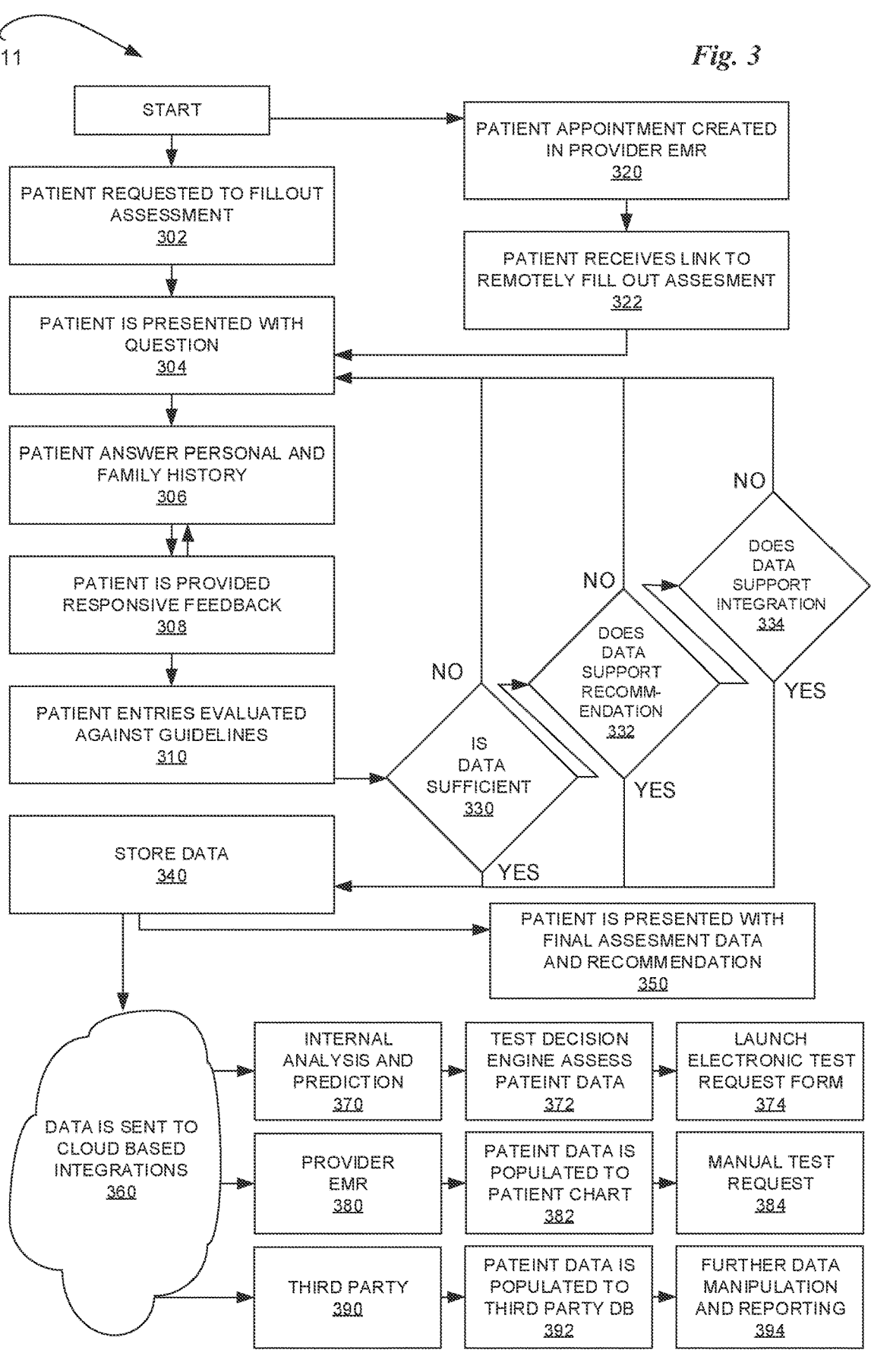
FIG. 3 is an algorithmic flow chart for using an assessment data collection engine and an assessment data analysis and prediction engine of the computing environment of FIG. 1 according to an embodiment of the subject matter disclosed herein.

FIG. 3 is an algorithmic flow chart of methods that span using the health care assessment data collection engine 111 and the healthcare data analysis and prediction engine 116 of the computing environment of FIG. 1 according to an embodiment of the subject matter disclosed herein. The algorithms presented in FIG. 3 are one embodiment of the overall health data collection and assessment systems and methods discussed herein. A skilled artisan understands that the arrangement and details of each step and/or component may vary without deviating from the spirit and scope of the novel methods and systems described herein.

With that, this embodiment of the algorithm begins at a start step when a patient wishes to engage an assessment. There are multiple paths for a patient to be presented with questions that are part of an assessment; two are shown in this embodiment. In one path, the patient may be simply interviewed, at step 302, by a clinician or physician who has access to a user interface for using the health care assessment data collection engine 111. Thus, as questions are presented, the clinician or physician may enter answers (assessment data) into health care assessment data collection engine 111 as discussed in further steps below. Alternatively, a patient may engage the system remotely at steps 320 and 322 by establishing a remote appointment having access to a provider EMR, whereupon a patient is presented with an electronic link to a user interface for answering questions as assessment components are presented. The link may be, for example, a hyperlink or other selectable element that may be clicked, tapped, or otherwise selected, and that directs a user to, for example, a software application or a networked webpage. In other paths not illustrated, a patient may fill out a paper or digital form themselves at the office of the provider and simply deliver the filled-out form via a paper copy or a digital form transfer. Such additional aspects may be facilitated by using a patient's personal computing device (e.g., mobile phone or tablet) that utilizes a QR code or other machine-readable code to initiate and finalize the process; the code may provide data that identifies one or more patients, healthcare providers, records, medical tests, procedures, or treatments, geographical locations, smart device identifiers, timestamps, etc.

Both of these paths lead to one or more questions being presented to a patient at step 304. Each question(s) may correspond to at least one component of the assessment component corresponding to the specific assessment. That is, the specific question being presented will depend upon the nature of the assessment (e.g., questions about family history with cancer is a component of a cancer assessment). In some embodiments, the initial questions presented may be numerous and have an initial set path so as to establish at least a baseline of data points for required components in an assessment. For example, specific questions about age, sex at birth, historical assessment data, past test results, and the like (e.g., personal and family history) may be required components of some assessments and can be presented and answered, generally speaking, at step 306. As each question or set of questions is inputted, the patient may be presented with responsive data at step 308 depending upon the nature and disposition of the answers given to questions in step 306. This responsive feedback may be prompts for additional or enhanced answers to questions or enhanced answers to questions. Further, the responsive feedback may be recursive in nature. That is, the patient may be given an opportunity to answer a specific question again. For example, when presented a question about family history of cancer, more than one family member may have a history with cancer and more than one type of cancer may be evident within the same family member worthy of inclusion as a data point (e.g., component) of the assessment. Thus, the arrows between these steps 306 and 308 represent the responsive feedback and recursive nature of these question-and-answer interactions between the patient and the health care assessment data collection engine 111.

Once a patient navigates through all iterative and recursive questions presented in the assessment survey, the collected data may be evaluated against one or more guidelines at step 310. This step may sometimes be referred to as a criteria check, as various determination may be made at this stage in analysis of the collected data. These specific evaluations may be made simultaneously, serially, or in any combination of pattern or order. Each determination may independent of each other and no one evaluation is dispositive such that any other evaluation is disrupted, interrupted, or bypassed. In the embodiment of FIG. 3, the method presents three different sets of guidelines for such determinations of the sufficiency of the collected data. These three decision points in the method are 1) an analysis as to whether the collected data is sufficient for the given assessment at step 330, 2) an analysis as to whether the collected data supports a health care recommendation at step 332, and 3) an analysis as to whether the collected data support integration into a data collection database that may be used for machine learning and influencing future recommendation analyses and assessment component manipulation at step 334. In this embodiment, if any of these decision points results in NO, the method loops back to a data collection phase at step 304. Similarly, in this embodiment, if any of these decision points results in YES, the method may proceed to a data storage phase at step 340. As is discussed next, each of these decision points may be assessed independent of each other such that simultaneous steps are carried out in different paths across the method of FIG. 3. Turning now to each decision point, specific criteria for answering YES or NO are presented.

In the first presented decision point 330, the collected data is analyzed with respect to its inherent completeness. That is, the initial questions as presented in the assessment may include required answers as part of any plausible recommendation to be gleaned from the collected data. If any questions are unanswered or not sufficiently answered, the decision at step 330 may force the patient to loop back and answer the question, either initially or a second time with a different or enhanced answer. For example, a user may enter a birthdate that does not make sense with respect to the assessment such as entering a birthdate indicating that the patient's age is less than 2-years-old, or entering data for a sex-at-birth question that does not comport with a purpose of the assessment (e.g., reproductive health assessment). As such, if the sufficiency of the collected data for the purposes of the assessment is just not complete enough, the method may revert to the survey again so as to remedy the insufficiency. In some embodiments, this initial insufficiency may cause the additional analysis decision points (e.g., decisions points 332 and 334) to be bypassed until the initial decision point 330 may be satisfied. In other embodiments, this initial insufficiency may have no effect on the additional analysis decision points 332 and 334.

In the next presented decision point 332, the collected data is analyzed with respect to satisfaction of one or more sets of criteria for making a healthcare recommendation such as a recommendation for a specific test or a specific prescription. That is, the collected data in the assessment may inform specific criteria that will trigger a recommendation of a specific path associated with the nature of the assessment. However, if any questions are unanswered or not sufficiently answered, the decision at step 332 may force the patient to loop back and answer the question, either initially or a second time with a different or enhanced answer to further inform the recommendation engine with regard to a health care decision. For example, a user may enter answers to specific familial history questions that do not provide a complete answer (for the purposes of a recommendation in this assessment) to the familial history questions. As such, if the sufficiency of the collected data for the purposes of the assessment is just not complete enough, the method may revert to the survey again so as to remedy the insufficiency. In some embodiments, this initial insufficiency may cause the additional analysis decision points (e.g., decisions points 330 and 334) to be bypassed until the recommendation decision point 332 may be satisfied. In other embodiments, this initial insufficiency may have no effect on the additional analysis decision points 330 and 334.

In the next presented decision point 334, the collected data is analyzed with respect to satisfaction of one or more sets of criteria for integrating the collected data into a database for machine learning such may influence future assessments and analyses. That is, the collected data in the assessment may inform specific criteria that will trigger an assimilation of the data into one or more databases that may be used in a feedback loop to affect how survey question are asked or the criteria for how decision points 330 and 332 are handled. Further, integration may also include sending data to an EMR provider or to third-party service providers. These specific integrations are discussed below further. However, if any questions are unanswered or not sufficiently answered, the decision at step 334 may force the patient to loop back and answer the question, either initially or a second time with a different or enhanced answer to further inform the recommendation engine with regard to a health care decision. In some embodiments, this initial insufficiency may cause the additional analysis decision points (e.g., decisions points 330 and 332) to be bypassed until the integration decision point 334 may be satisfied. In other embodiments, this initial insufficiency may have no effect on the additional analysis decision points 330 and 332.

After one or more decision points 330, 332, and/or 334 being satisfied as YES, the method may then step to several additional simultaneous paths for presentation, recommendation regarding, and/or integration/assimilation of, the collected data. In a first path after a YES decision, the patient may be presented directly with the collected data and any recommendation of a health care option at step 350. Such a presentation may likely be through an electronic interface such as display on a computing device or sending an email or other message via a credentialed platform. Additionally, or in lieu of, the directly presented data, the collected data and/or specific recommendation may be sent, as represented as a cloud step 360, to an integration cloud that may be part of the healthcare analysis and prediction engine 116. Within this "cloud", several additional paths may present as the analysis points of the collected data may inform differing paths. To this end, logical and programmatic decision blocks may initiate one or more of the actions as shown in horizontal rows of steps. These may each be taken independently and/or simultaneously depending on the satisfaction of specific triggering criteria within the healthcare analysis and prediction engine 116. As is discussed next, the paths may be generally delineated as 1) an internal use path, 2) a provider-partner path, and 3) a third-party partner path.

In a first integration path, additional internal-use recommendations may be made via an internal analysis and prediction engine at step 370. Thus, the collected data may be analyzed here after storage at step 350 so as to generate a specific recommendation of a health care path via a test decision engine step 372. Such recommendation decision may be made here in addition to or in lieu of any path undertaken after the decision point 332 as discussed above.

Of specific note, if the recommendation is undertaken here at the integration stage, an immediate electronic test request form may be presented, at step 374, to the patient so as to streamline the process of undertaking the recommended healthcare path.

Similarly, in a second integration path, recommendations may be made using any analysis and prediction engine at step 380 to a provider partner though use of an EMR of the patient. Thus, the collected data may be analyzed here after storage at step 350 so as to generate a specific recommendation of a health care path. Such recommendation decision may be made here in addition to or in lieu of any path undertaken after the decision point 332 as discussed above. Of specific note, if the recommendation is undertaken here at the integration stage, the patient's EMR is updated, at step 382, at the partner-provider facility and the provider may initiate a proprietary electronic test request or a manual test request at form at step 384, to the patient so as to streamline the process of undertaking the recommended healthcare path.

Again, similarly, in a third integration path, recommendations may be made using any analysis and prediction engine at step 390 to a third-party partner though use of third-party database. Thus, the collected data may be analyzed here after storage at step 350 so as to generate a specific recommendation of a health care path. Such recommendation decision may be made here in addition to or in lieu of any path undertaken after the decision point 332 or 334 as discussed above. Of specific note, if the recommendation is undertaken here at the integration stage, the third-party database is updated, at step 392, at the third-party partner facility and the third-party partner may initiate assimilation, data manipulation, data reporting or any other third-party task worthy of undertaking at step 394.

The foregoing description of steps with the method depicted in FIG. 3 includes aspects undertaken by several different computing devices as depicted in FIG. 1. Delineations between differing computing devices may be less important when considering the flow of the steps within the myriad method available with permutations of the methods depicted in FIG. 3. Further, differing blocks and components within the method depicted in FIG. 3 may be further nuanced and abstracted though nested routines and subroutines depending on the nature of any given underlying assessment. As such, several different overarching workflows may be integrated within or otherwise grafted to the base-level methods depicted in FIG. 3. FIGS. 4-7 are four different examples of workflows that may utilized within the system of methods described with respect to FIGS. 1-3.

Figure 4:
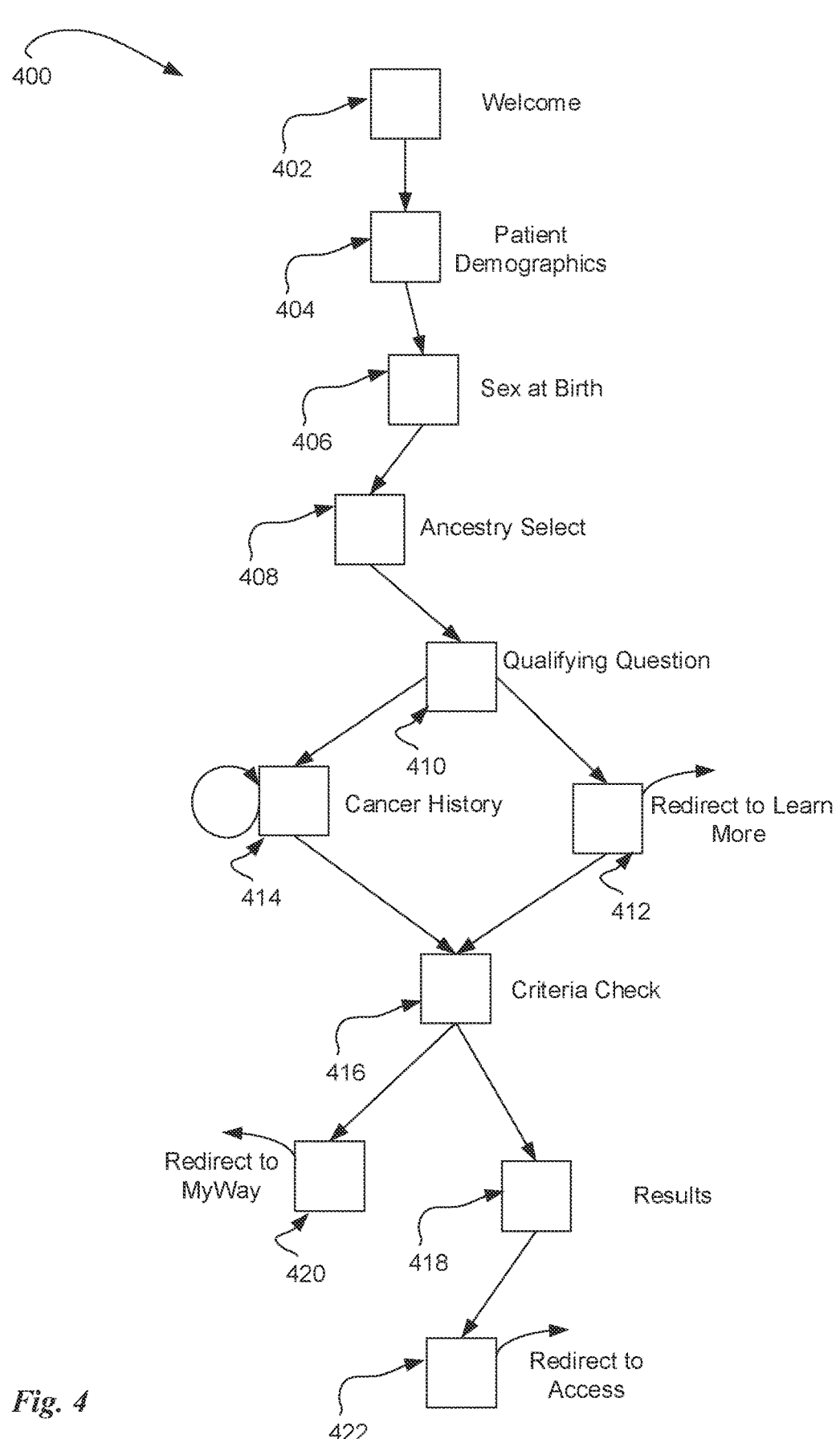
FIG. 4 is a workflow diagram illustrating components a first embodiment of a workflow that can be implemented with the systems and methods of FIG. 1-3 according to an embodiment of the subject matter disclosed herein.

FIG. 4 is a workflow diagram illustrating components of an embodiment of a workflow 400 that can be implemented with the systems and methods of FIG. 1-3 according to an embodiment of the subject matter disclosed herein. In this workflow 400, or any workflow, components for specific assessment may be customized to fit specific assessment needs and specific needs of a provider partner as needed. Further, the narrative and specific nomenclature for questions surrounding each component may be customized to suit needs. Further yet, the workflows may be dynamic in that the nature and flow of the workflow can be dynamically and recursively altered in response to specific answers to specific questions, e.g., "are you trying to become pregnant," "are you concerned about a specific cancer," and the like. As such, specific recommended paths may be realized and recommended in addition to further enhancing activities such as presentation of educational modules and materials, videos, animations that may be AAA accessible, ADA compliant and geared for patients of all ages and abilities.

In the embodiment depicted in FIG. 4, the workflow 400 begins with a welcome component 402 that may provide introductory and overview remarks to a patient about to complete the assessment survey that is part of the workflow 400. As one might expect, an initial component of the workflow 400 may be to collect patient demographics 404 such as age, height, weight, and cursory data about additional demographics so as to establish a patient record with respect to the underlying assessment. A follow-on component may be to determine sex at birth 406 in a next component of the workflow 400. Further, an ancestry selection component 408 may also be included in an initial set of questions for continuing to establish an initial patient record within the assessment workflow.

To this point, these initial questions/components may be presented in a serial manner in a stepwise manner. As questions transition into having more than one answer or more than one set of answers, the serial manner of the workflow 400 may diverge into multiple simultaneous paths with recursive branches and/or dynamically shifting branches. Such a component having a recursive or dynamic opportunity is simply referred to as a qualifying question 410. An example of a qualifying question here may be familial and/or hereditary history with respect to cancer diagnoses. Thus, an individual patient may have more than one family member with a history of cancer thereby necessitating a recursively answerable component to capture the multiple answers. Such a recursively answerable component may be depicted as the cancer history component 414 with looped arrow to the side indicating the recursive nature of answering this component.

Further, the individual patient may have a specific answer to a specific question that triggers an immediate dynamic response as indicated by a curved-out arrow. In the component 412, a specific answer may trigger a dynamic workflow response to learn more through an additional and separate workflow. Thus, the workflow may trigger a separate and simultaneous redirect to a related "Learn more" workflow (not shown in the FIGs.). Notwithstanding any sperate dynamically invoked workflows, after all recursive and dynamic components are satisfied, the workflow may proceed to a component for criteria check 416. Here, the workflow may assess all answers to this point to determine if enough data or specific data has been collected worthy of undertaking a recommended health care path. If the collected data triggers a specific recommendation suitable to be handled by a third party, the workflow may proceed to a redirect to "My Way" component 420, whereupon a third-party service is invoked to initiate paperwork and/or an electronic request for a specific recommended test. Simultaneously, the collected data to this point may also be assembled in a results component 418 whereupon the collected data may be packaged and sent to an internal assimilation database for possible influence over future recommendations at a redirect to Access component 422.

Figure 5:
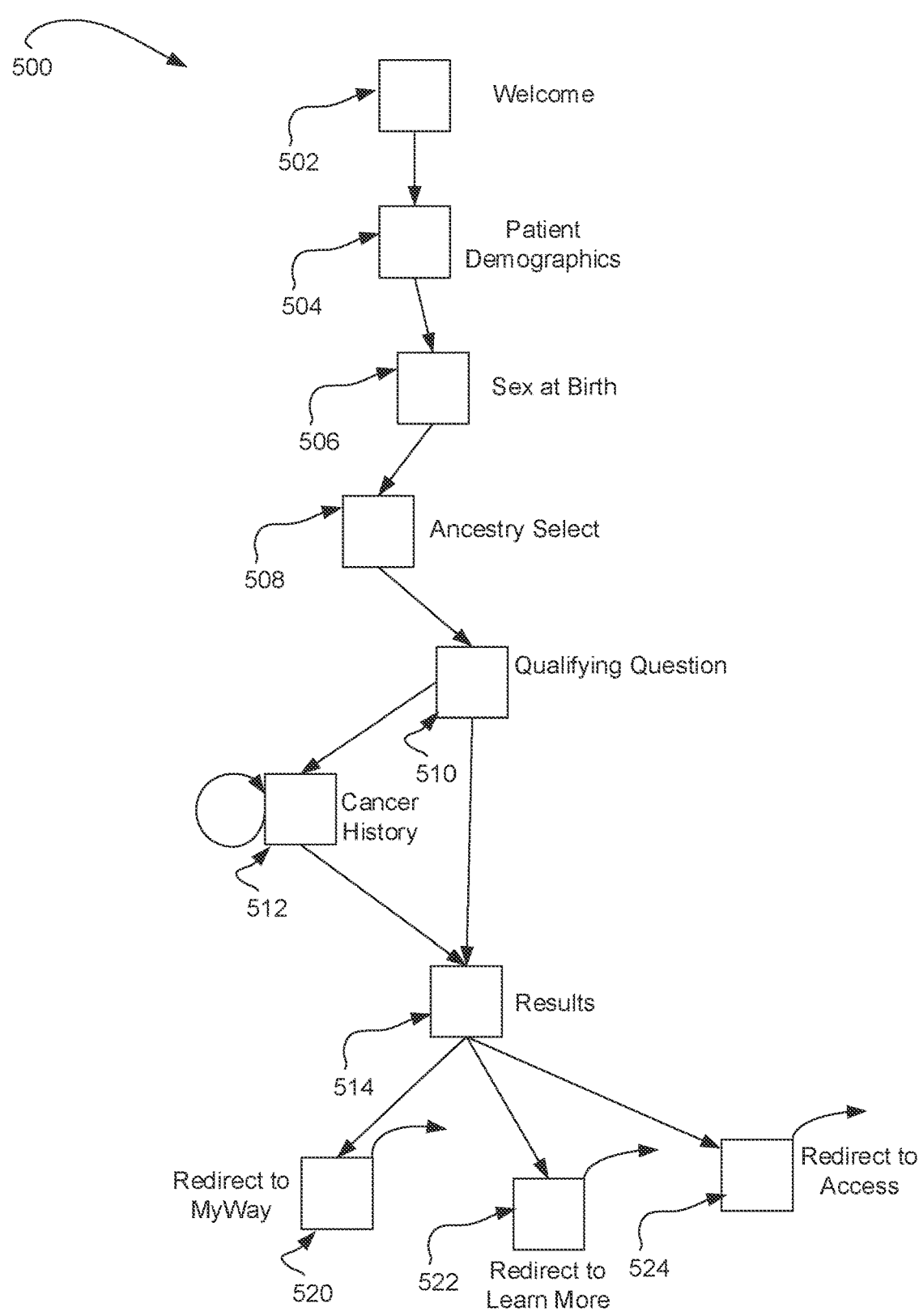
FIG. 5 is a workflow diagram illustrating components of another embodiment of a workflow that can be implemented with the systems and methods of FIG. 1-3 according to an embodiment of the subject matter disclosed herein.

FIG. 5 is a workflow diagram illustrating components of another embodiment of a workflow that can be implemented with the systems and methods of FIG. 1-3 according to an embodiment of the subject matter disclosed herein. In the embodiment depicted in FIG. 5, the workflow 500 begins with a welcome component 502 that may provide introductory and overview remarks to a patient about to complete the assessment survey that is part of the workflow 500. As before, an initial component of the workflow 500 may be to collect patient demographics 504 such as age, height, weight, and cursory data about additional demographics so as to establish a patient record with respect to the underlying assessment. A follow-on component may be to determine sex at birth 506 in a next component of the workflow 500. Further, an ancestry selection component 508 may also be included in an initial set of questions for continuing to establish an initial patient record within the assessment workflow.

To this point, these initial questions/components may be presented in a serial manner in a stepwise manner. As questions transition into having more than one answer or more than one set of answers, the serial manner of the workflow 500 may diverge into multiple simultaneous paths with recursive branches and or dynamically shifting branches. Such a component having a recursive or dynamic opportunity is simply referred to as a qualifying question 510. An example of a qualifying question here may be familial and/or hereditary history with respect to cancer diagnoses. Thus, an individual patient may have more than one family member with a history of cancer thereby necessitating a recursively answerable component to capture the multiple answers. Such a recursively answerable component may be depicted as the cancer history component 514 with looped arrow to the side indicating the recursive nature of answering this component.

After all recursive components are satisfied, the workflow may proceed to a component for assembling results 514. Here, the workflow may assess all assembled resulting answers to determine the collected data is worthy of undertaking a recommended health care path, e.g., a dynamic path as indicated by curved arrows out of various components. If the collected data triggers a specific recommendation suitable to be handled by a third party, the workflow may proceed to a redirect to "My Way" component 520, whereupon a third-party service is invoked to initiate paperwork and/or an electronic request for a specific recommended test. Simultaneously, the collected data may be packaged and sent to an internal assimilation database for possible influence over future recommendations at a redirect to Access component 524 Further yet, the individual patient may have a specific answer to a specific question that triggers an immediate dynamic response to redirect to a related "Learn more" workflow (not shown in the FIGs.).

Figure 6:
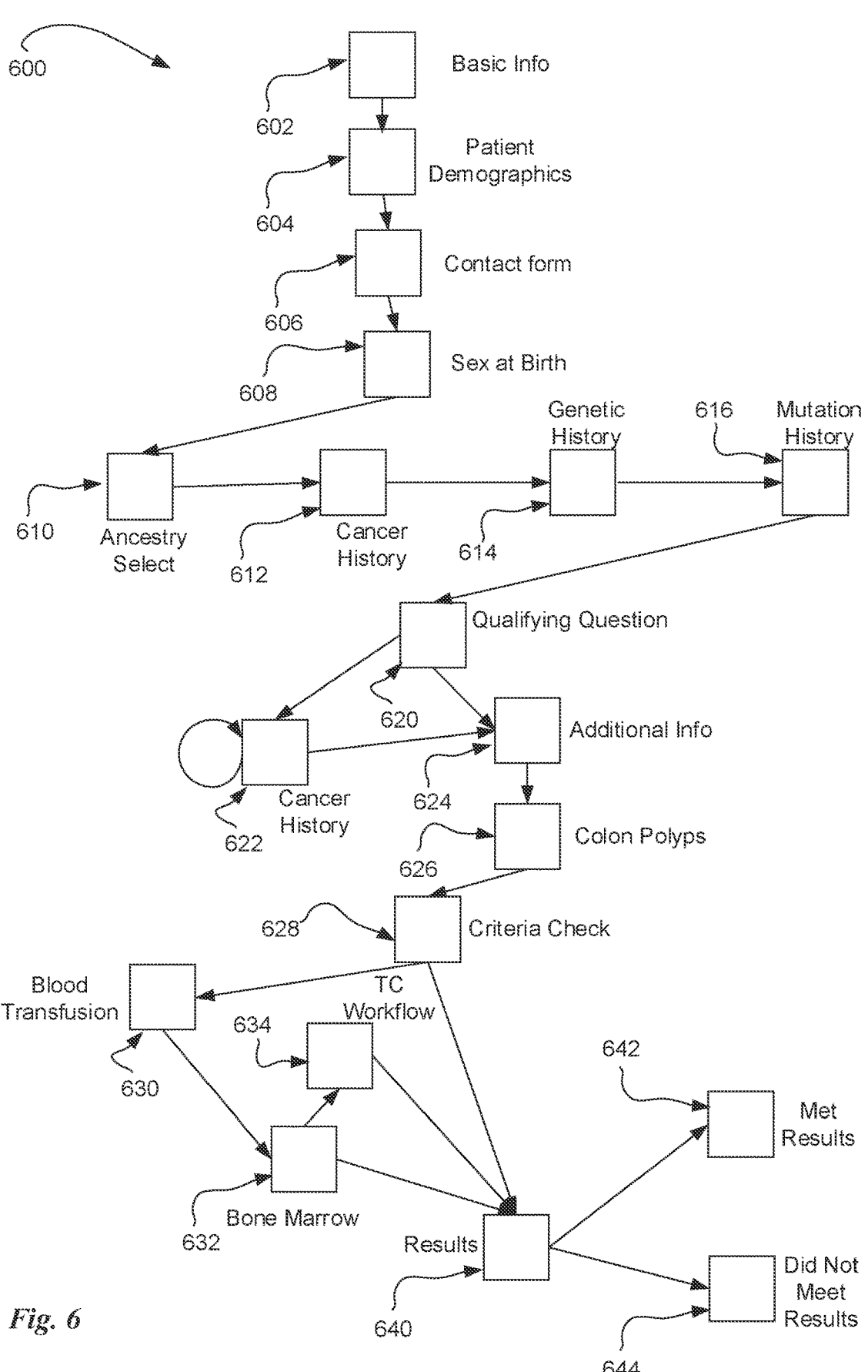
FIG. 6 is a workflow diagram illustrating components of another embodiment of a workflow that can be implemented with the systems and methods of FIG. 1-3 according to an embodiment of the subject matter disclosed herein.

FIG. 6 is a workflow diagram illustrating components of another embodiment of a workflow that can be implemented with the systems and methods of FIG. 1-3 according to an embodiment of the subject matter disclosed herein. In the embodiment depicted in FIG. 6, the workflow 600 begins with a basic information collection component 602 that may provide introductory and overview remarks to a patient about to complete the assessment survey that is part of the workflow 600. As before, a next component of the workflow 600 may be to collect patient demographics 604 such as age, height, weight, and cursory data about additional demographics so as to establish a patient record with respect to the underlying assessment. A follow-on component may be to determine contact information 606 for the patient in a next component of the workflow 600. Another follow-on component may be to determine sex at birth 608 in a next component of the workflow 600. Further, an ancestry selection component 610 may also be included in an initial set of questions for continuing to establish an initial patient record within the assessment workflow 600. In this workflow 600, additional basis follow-on question components may also be posed such as initial cancer history 612, initial genetic history 614, and initial mutation history 616.

To this point, these initial questions/components may be presented in a serial manner in a stepwise manner. As questions transition into having more than one answer or more than one set of answers, the serial manner of the workflow 600 may diverge into multiple simultaneous paths with recursive branches and or dynamically shifting branches. Such a component having a recursive or dynamic opportunity is simply referred to as a qualifying question 620. An example of a qualifying question here may be familial and/or hereditary history with respect to cancer diagnoses. Thus, an individual patient may have more than one family member with a history of cancer thereby necessitating a recursively answerable component to capture the multiple answers. Such a recursively answerable component may be depicted as the cancer history component 622 with looped arrow to the side indicating the recursive nature of answering this component. After the initial qualifying question component 620 and/or all recursive cancer history component 622 questions, an additional information component 624 may also be presented to collect any additional information suited for this assessment. Further yet, as this assessment may be directed to colon cancer, the presence of lack thereof regarding colon polyps may be determined at component 626.

Notwithstanding any sperate recursively invoked workflows, after all recursive and serial components are satisfied, the workflow may proceed to a component for criteria check 628. Here, the workflow may assess all answers to this point to determine if enough data or specific data has been collected worthy of undertaking a recommended health care path. If the collected data triggers a specific additional data collection path, the workflow may proceed to a blood transfusion recommendation component 630 followed by a bone marrow test at component 632. This path then invokes a dynamic workflow component, TC workflow 634 before sending all collected data and invoked procedures and tests to a results component 636. Simultaneously, the collected data to this point may also be assembled in a results component 418 whereupon the collected data may be packaged and sent to an internal assimilation database for possible influence over future recommendations at a redirect to Access component 422. After all recursive components and serial components are satisfied, the workflow may proceed to a component for assembling results 640. Here, the workflow may assess all assembled resulting answers to determine the collected data has "met results" at component 642 or has "not met results" at component 644. These conclusory assessments may be communicated, assimilated, integrated, or otherwise used within any system or method heretofore described.

Figure 7:
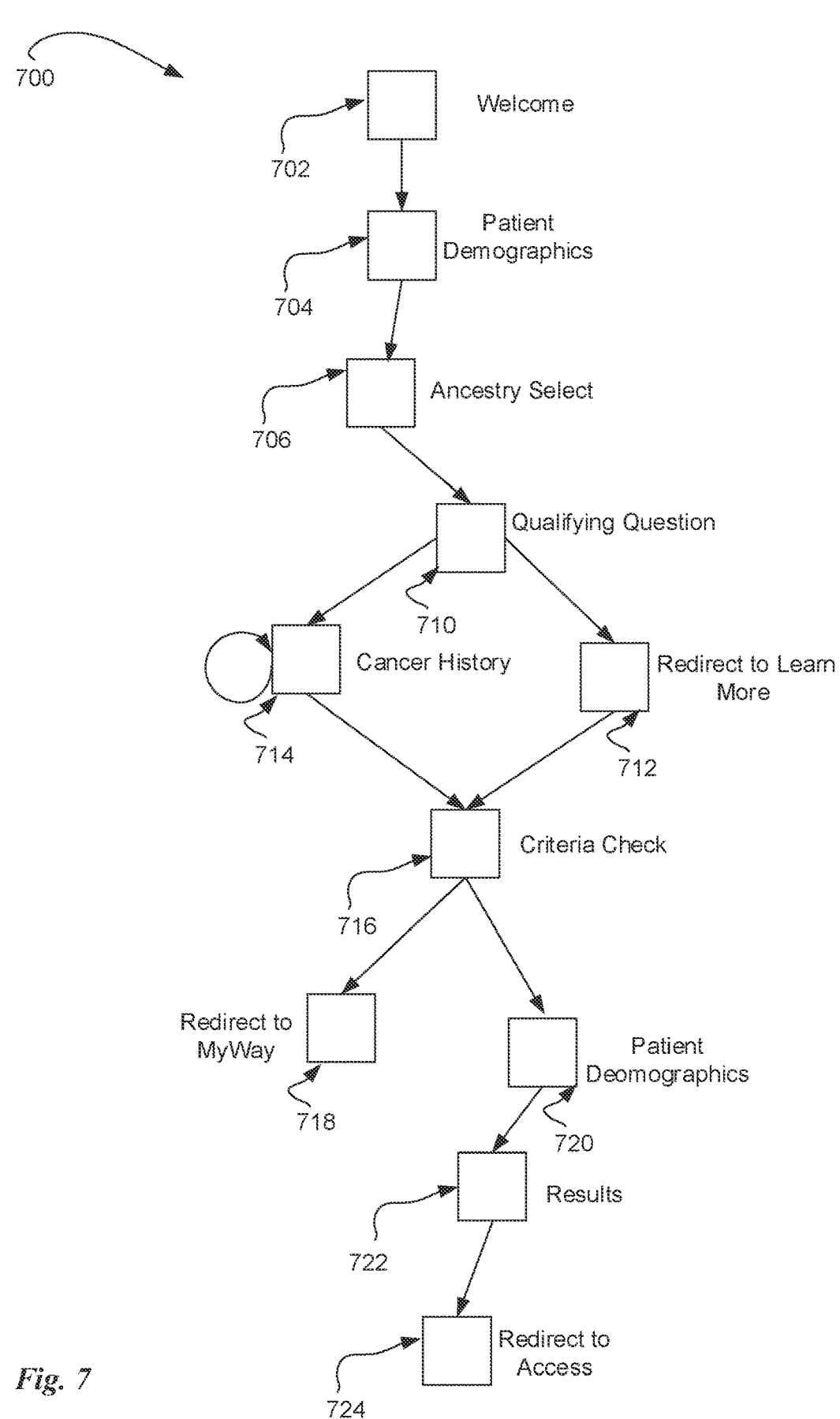
FIG. 7 is a workflow diagram illustrating components of another embodiment of a workflow that can be implemented with the systems and methods of FIG. 1-3 according to an embodiment of the subject matter disclosed herein.

FIG. 7 is a workflow diagram illustrating components of another embodiment of a workflow that can be implemented with the systems and methods of FIG. 1-3 according to an embodiment of the subject matter disclosed herein. In the embodiment depicted in FIG. 7, the workflow 700 begins with a welcome component 702 that may provide introductory and overview remarks to a patient about to complete the assessment survey that is part of the workflow 700. An initial component of the workflow 700 may be to collect patient demographics 704 such as age, height, weight, and cursory data about additional demographics so as to establish a patient record with respect to the underlying assessment. A follow-on component may be to determine sex at birth 706 in a next component of the workflow 700. Further, an ancestry selection component 708 may also be included in an initial set of questions for continuing to establish an initial patient record within the assessment workflow.

To this point, these initial questions/components may be presented in a serial manner in a stepwise manner. As questions transition into having more than one answer or more than one set of answers, the serial manner of the workflow 700 may diverge into multiple simultaneous paths with recursive branches and or dynamically shifting branches. Such a component having a recursive or dynamic opportunity is simply referred to as a qualifying question 710. An example of a qualifying question here may be familial and/or hereditary history with respect to cancer diagnoses. Thus, an individual patient may have more than one family member with a history of cancer thereby necessitating a recursively answerable component to capture the multiple answers. Such a recursively answerable component may be depicted as the cancer history component 714 with looped arrow to the side indicating the recursive nature of answering this component.

Further, the individual patient may have a specific answer to a specific question that triggers an immediate dynamic response as indicated by a curved-out arrow. In the component 712, a specific answer may trigger a dynamic workflow response to learn more through an additional and separate workflow. Thus, the workflow may trigger a separate and simultaneous redirect to a related "Learn more" workflow at component 712 (not shown in the FIGs.). Notwithstanding any sperate dynamically invoked workflows, after all recursive and dynamic components are satisfied, the workflow may proceed to a component for criteria check 716. Here, the workflow may assess all answers to this point to determine if enough data or specific data has been collected worthy of undertaking a recommended health care path. If the collected data triggers a specific recommendation suitable to be handled by a third party, the workflow may proceed to a redirect to "My Way" component 718, whereupon a third-party service is invoked to initiate paperwork and/or an electronic request for a specific recommended test. Simultaneously, the collected data to this point may also be supplemented with additional patient demographic data that may be triggered by specific answers to previous component questions at component 720. Then all collected data is assembled in a results component 722 whereupon the collected data may be packaged and sent to an internal assimilation database for possible influence over future recommendations at a redirect to Access component 724.

Figure 8:
FIG. 8 is a method flow chart illustrating an exemplary computer-based method for establishing a trained prediction model and updating the trained prediction model to generate healthcare recommendations according to an embodiment of the subject matter disclosed herein.

FIG. 8 is a method flow chart illustrating an exemplary computer-based method for establishing a trained prediction model and updating the trained prediction model to generate healthcare recommendations according to an embodiment of the subject matter disclosed herein. In this block diagram, some modules may represent functional activities, such as data collection and training, but this diagram is, nevertheless, presented in a block diagram format to convey the functional aspects of the overall analysis and prediction computing block 116 of FIG. 1. Thus, in FIG. 8, a first aggregated set of functions includes the upper half 801 of the diagram where a predictive model is first established and trained for use in making predictions. Once the trained model 830 is established, the lower half 802 of the block diagram of FIG. 8 focuses on generating initial predictions to be checked against expected or historical data as well as new predictions based on new data collected.

In the upper half 801, training data 810 may be drawn from an established database of known and established healthcare recommendations based on already collected historical assessment data with an initialized model form 815. The training data is then fed to a training engine 820 to begin establishing the trained model to be used for predictions and recommendations for health care decisions. The training data may include actual collected data from historical records of a patients or may be scientific studies with best-known practices at the time of training. Further, the training data may be created based on learned judgment of best medical practices. This model form 815 is simply an initial "best guess" by administrators of the healthcare data collection and analysis system. As the initial training data 810 may also include outcomes such as healthcare recommendations and predictions, a training engine 820 may begin to "train" the model form 815 by identifying specific data correlations and data trends that affect the effectiveness and accuracy of predictions and recommendations from the training data 815. As all relevant and/or influential correlations are determined by the training engine 820, a trained model 830 is established.

With the trained model 830 established, an inference engine 850 may then utilize the trained model 830 along with newly collected assessment data. That is, a clinician or physician may wish to use the system 100 to enhance, verify, or otherwise generate healthcare recommendations (e.g., prescriptions, tests, therapeutics, and the like) based on collected assessment data. Therefore, the system may present new data 860 in the form of collected assessment data. The new data 860 is used by the inference engine 850 that employs use of the trained model 830 to generate one or more recommendations 855.

The types and varieties of data that can be used as inputs to the overall healthcare assessment data recommendations and prediction system are vast. As a general rule, all collected data as described above with respect to all components in any one of the assessment models of FIGS. 4-7 may be used as new data 860. However, as time goes on and the inference engine 850 changes with respect to additional results data 831 being fed back through the system for learning purposes, some components may begin to have less influence over the recommendations and predictions (e.g., the machine learns that some components exhibit little or no correlation to results of recommendations and/or predictions). Other components may exhibit greater influence over the success of healthcare recommendations and predictions. As results data 831 are assimilated, weighting factors may begin to emerge regarding the components used in assessment collection practice.

As discussed above, the inference engine 850 may be used to generate predicted outcomes based on new data that is entered as well as based on a trained model 830 established previously from training data 810. Each of the recommendations and predictions discussed below may be influenced by one or more components as discussed above. Further, algorithms may be developed for one or more predicted outcomes based on weightings given to each of the influential inputs. In general, any set of components may have weightings that influence any predicted outcome.

Figure 9:
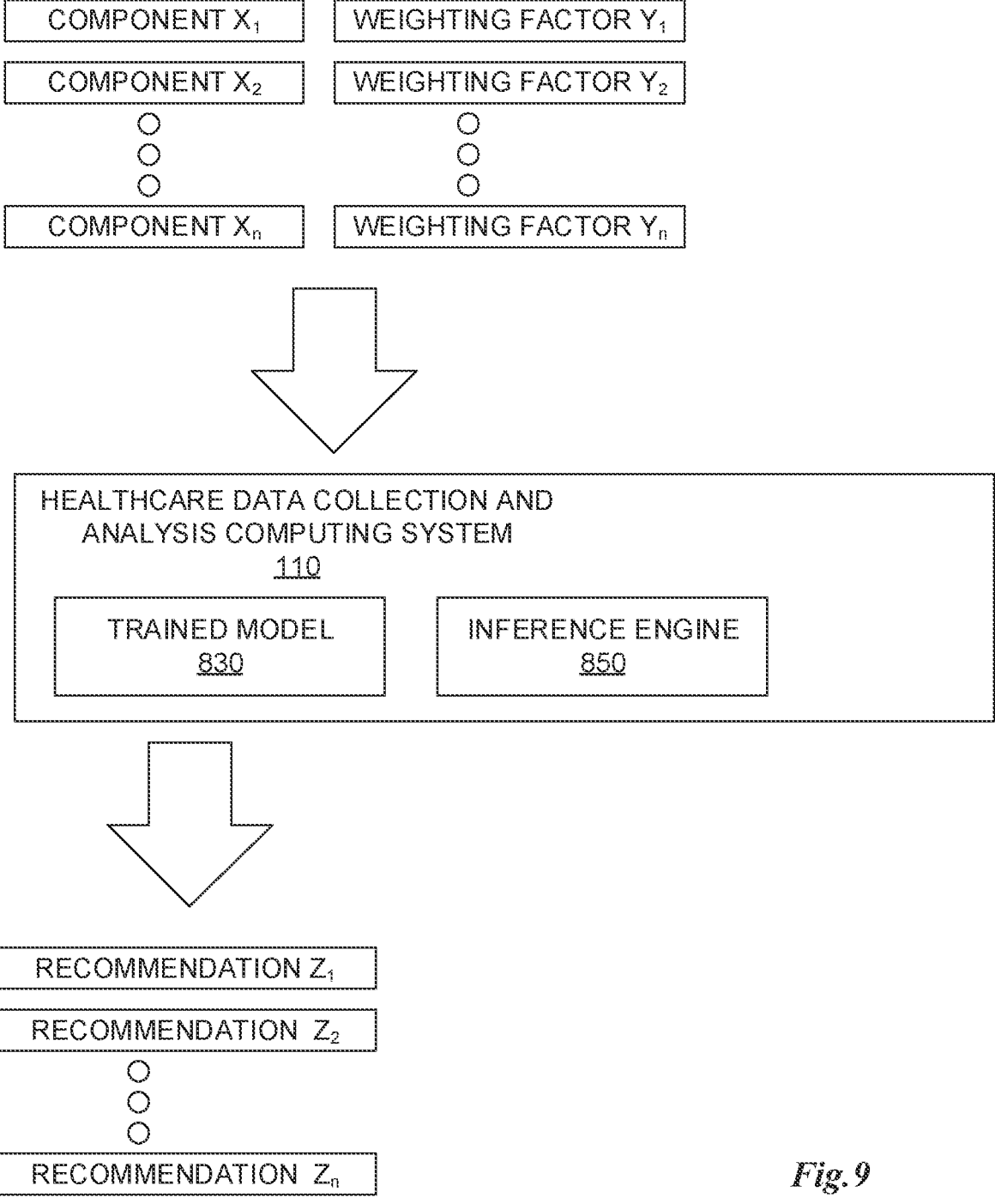
FIG. 9 is a method flow chart illustrating an exemplary computer-based method for utilizing a trained prediction model and delivering matched recommendations based upon a trained prediction model according to an embodiment of the subject matter disclosed herein.

FIG. 9 is a method flow chart illustrating an exemplary computer-based method for utilizing a trained prediction model and delivering matched recommendations based upon a trained prediction model according to an embodiment of the subject matter disclosed herein. In general, all components that may be used to determine one or more recommendations or predictions are illustrated and discussed with respect to FIGS. 4-7, while all outcomes and predictions are illustrated in a bottom portion of FIG. 8. FIG. 9 illustrates one or more algorithms that may be realized during the establishment of the trained model 830 whereby the healthcare data collection and analysis server 110 may establish specific recommendations $Z_1$-$Z_n$ based on new data through its inference engine 850. That is, given inputs $X_1$-$X_n$, each with corresponding weighting factors $Y_1$-$Y_n$, the inference engine 850 will utilize the trained model to generate predicted outputs $Z_1$-$Z_n$. Generally speaking, the weighting factors may be a result of the prediction process whereby different factors are determined to be more or less influential over the prediction processes. For example, initial weighting factors may be zero as there does not exist any predictive data yet—but as predictions emerge and comparisons to reality are determined, weightings of influential factors may also emerge. These concepts may be better understood with respect to the following non-limiting examples.

Figure 10:
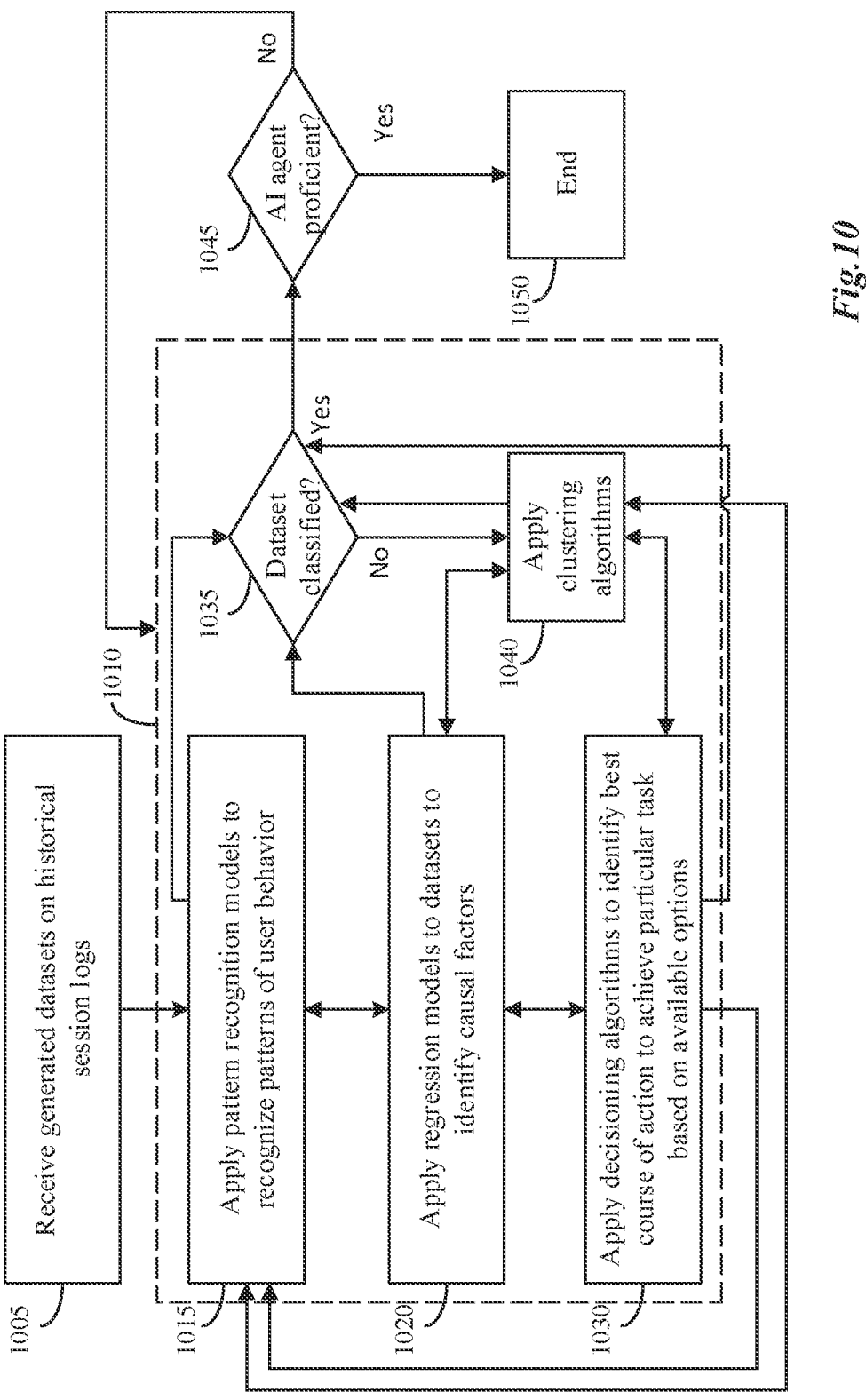
FIG. 10 is a flow diagram of an example process for training an artificial intelligence agent that may be executed to perform one or more operations described herein, in accordance with one or more example implementations.

FIG. 10 provides a machine-learning (ML) framework for embodiments of the predictive model disclosed herein. The ML predictive model may be configured to receive data on patient interactions and responses, and identify subsequent interactions and queries to be presented to the patient. Additionally or alternatively, the ML predictive model (or a second model) may be configured to receive responses, and provide predicted tests or procedures. To train the ML predictive model, one or more training datasets may be generated. Various machine-learning techniques may be applied to the training datasets to generate one or more models to be used. The models may be updated by generating updated training datasets, as more data becomes available, and re-training the models using the updated training datasets. The process of updating the predictive models may happen periodically (e.g., every day, week, or month), may occur when a certain minimum amount of data has become available (e.g., data for a minimum number of additional patients, such as 5, 10, 25, or 50), or may occur when any new data becomes available.

The frequency of model re-training may be inversely proportional to the size of datasets (how much total data is) available for re-training, such that if relatively less data that is available, the model may be updated more often, whereas if relatively more data that is available, the model may be updated less frequently. That is, if the model had already been trained on sufficiently robust datasets, then it may be less of a priority to re-train the model because the robust datasets are less likely to be affected by relatively few additional data points, whereas if the model had previously been trained on relatively sparse datasets, then it may be more likely to benefit from retraining using more data. There may be two reasons for this approach to updating the model. First, the less data that is available on prior experiences, the more impactful or relevant new data on new experiences may be. For example, as a hypothetical example, if there are a total of five experiences, adding a sixth experience to the training data may result in a significant change to model parameters, whereas if there are a total of 1000 experiences, adding another experience to bring the total to 1001 tends to be less likely to result in a significant change to the model parameters. Second, the more data that is available, the more computationally intensive the re-training process would be, and on balance, the costs of more frequent retraining may not be justified by the incremental gains obtained from adding, for example, the one thousand and first experience.

In various embodiments, one or more training datasets may comprise interaction data on how subjects interacted with different queries, pages, choices, etc. Interaction of subjects may be measured in various ways, such as time taken to respond to queries, lengths of responses, the substance of the responses, or characteristics or metadata about aspects of the interactions. The training datasets may additionally include health data based on the electronic health records (EHR) of subjects, such as patient diagnoses, conditions, visits to the clinic, screening tests, medical procedures, family history, etc. One or more machine learning techniques may be applied to the training datasets. In certain supervised learning techniques, for example, the health data may be a source of labels corresponding to the interaction data.

The artificial intelligence agent can include one or more trained machine-learning models (which may be executed by, e.g., healthcare data collection and analysis computing system 110 or other computing system) to carry out any of the functionality described herein. For example, the artificial intelligence agent can include trained regression, pattern recognition, or classification models that can identify or determine relationships between different users based on interaction data and health data. The machine-learning models of the artificial intelligence agent can be trained (e.g., by the healthcare data collection and analysis computing system 110) by performing a training process based on a set of session logs corresponding to the interaction of a cohort of subjects with a user interface.

Some examples of machine learning models can include neural networks (e.g., a deep neural network (DNN), a convolutional neural network (CNN), a recurrent neural network (RNN) such as a long short-term memory (LSTM) model, combinations thereof, etc.), trained regression models (e.g., linear regression, sparse vector machine (SVM) models, logistic regression, polynomial regression, ridge regression, Lasso regression, Bayesian linear regression, etc.), or other types of classifiers (e.g., naïve Bayes, decision trees, k-nearest neighbors (kNN), extreme gradient boost (XGBoost) models, etc.). The artificial intelligence agent can further include unsupervised machine-learning models. The aforementioned machine-learning models may also be utilized for any type of machine-learning or artificial intelligence performed task described herein.

The artificial intelligence agent can be trained using any suitable machine-learning training technique. For example, the artificial intelligence agent can be trained using supervised learning techniques, unsupervised learning techniques, or semi-supervised learning techniques. In an embodiment, the healthcare data collection and analysis computing system 110 may train the artificial intelligence agent using sets of training data.

Referring to FIG. 10, illustrated is a process 1000 of an example approach for applying various models to the generated datasets for training an artificial intelligence agent to reach a certain proficiency level (e.g., accuracy threshold, etc.), according to potential embodiments. Process 1000 may be implemented by any computing system or any other computing device described herein that may be used to implement a machine-learning platform for model training. Input of which models to use, or of the modified models to be used, to generate the datasets also may be received via a network (e.g., network 125) from one or more computing systems or user devices. At 1005, the computing system may receive generated datasets on historical session logs corresponding to subjects engaging with the user interface. The sessions may be monitored or accessed by the healthcare data collection and analysis computing system (e.g., from records of electronic activity generated by various user devices of different entities and their interactions, etc.). In some implementations, the generated datasets are created by sorting, categorizing, extracting, and/or manipulating acquired data from the sessions or from other electronic activity detected or received via the network.

After step 1005, process 1000 proceeds to 1010, where the computing system may apply machine-learning techniques to train the artificial intelligence agent. The machine-learning techniques may be executed by one or more processors of the computing system and may be updated via input from one or more user devices, such as an administrator device that manages the computing system or coordinates its operations in some capacity. The algorithms may encompass a variety of machine-learning techniques that are executed by the computing system to train one or more trainable parameters of the machine-learning models described herein. For example, the artificial intelligence model can be trained utilizing various input data, such may include information extracted from one or more medical health records.

At 1015, in an embodiment, the computing system may apply pattern recognition algorithms to recognize patterns of user behavior. Regression algorithms may be applied by the primary computing system, for example, to identify causal factors (reasons) for one or more interactions (step 1020). For example, at 1020, regression algorithms may be employed to train the artificial intelligence on one or more trainable parameters that indicate whether a certain interface or query should be presented or certain information sought. Some examples of regression techniques that may be used by the artificial intelligence agent include linear regression models, logistic regression models, SVM techniques, Least Absolute Selection Shrinkage Operator (LASSO) regression models, polynomial regression models, and other regression tree models. At 1030, the computing system may apply decisioning algorithms to identify a best course of action suited to achieve a particular task based on one or more available options (e.g., to determining whether a screening test should be performed based on available information).

At 1040, if the artificial intelligence agent cannot determine whether to a query should be presented (e.g., a confidence score generated by the artificial intelligence agent is less than a predetermined threshold) (step 1035), the computing system may apply clustering algorithms to employ additional machine-learning techniques to classify interaction data and/or health data into a nearest related cluster in a set of health records. The number of clusters may be communicated to the computing system from an administrative computing device via the network to limit or expand the training of the artificial intelligence agent, or may be variable depending on the data acquired from the historical sessions of the various subjects corresponding to the health records. In some embodiments, the number of clusters can be predetermined so as to fit the tasks from the historical sessions and interaction data of subjects into a preferred number of clusters. In various embodiments, the cubic clustering criterion (CCC) statistic may be calculated (from SAS procedure FASCLUS) to determine the maximum number of clusters to allow for training the artificial intelligence agent.

In some implementations, interactions with the user interface can be categorized using a k-means clustering algorithm that is unsupervised, with no dependent variable associated therewith. Alternatively or additionally, other approaches can be used to detect a sequence or pattern of behavior in the interactions of subjects who received certain screening tests. For example, LSTM recurrent neural networks, gradient boosted trees, logistic regression, hidden and basic Markov models, and frequent pattern growth algorithms may be utilized in classifying patterns and decisions while training the artificial intelligence agent.

In some embodiments, clusters may be developed using, for example, Python, SAS, R, Spark and/or H2O. In certain versions, k-means clustering may be developed using the SAS FASTCLUS procedure, which performs a disjoint cluster analysis on the basis of distances computed from one or more quantitative variables. The observations (e.g., potentially common characteristics of subjects) may be divided into clusters such that every observation belongs to one and only one cluster. The clusters do not form a tree structure. The FASTCLUS procedure uses Euclidean distances, so the cluster centers are based on least-squares estimation. This kind of clustering method is often called a k-means model. The clustering aims to partition n observations into k clusters in which each observation belongs to the cluster with the nearest mean. The final cluster centers are the means of the observations assigned to each cluster when the algorithm is run to complete convergence. Each iteration reduces the least-squares criterion until convergence is achieved.

For example, given a set of observations $(x_1, x_2, \ldots, x_n)$, where each observation is a d-dimensional real vector, k-means clustering aims to partition the n observations into $k(\leq n)$ sets $S=\{S_1, S_2, \ldots, S_k\}$ so as to minimize the within-cluster sum of squares ("WCSS") (i.e., variance). Formally, the objective is to find:

$$\arg \min \sum_{i=1}^{k} \sum_{k \in S_i} \|x - u_i\|^2 \qquad \text{Eq. 1}$$

where $\mu_i$ is the mean of points in $S_i$.

While the computing system executes the machine-learning techniques, one technique may be applied (such as at 1015) before a different type of machine-learning technique is carried out (such as at 1020). Instead of proceeding to 1030, however, it may be needed to apply the same machine-learning technique used before (such as repeating 1015) to make a new decision or after discovering a new situation of user interaction (which is represented by the double arrows between different steps in process 1000). For example, process 1000 may continue to step 1035 to check whether a dataset is classified after 1015, 1020, 1030, or 1040. In some embodiments, after step 1030 is executed, process 1000 may continue to 1015, 1020, or 1040 for further training instead of continuing to step 1035. In other embodiments, 1040 is executed before checking whether the dataset is classified at 1035 (e.g., 1015 continues to 1040 and/or 1020 continues to 1040). Additionally, after clustering algorithms are applied at 1040, process 1000 may continue to 1015, 1020, 1030, or immediately recheck whether the dataset is classified by proceeding to 1035, in some examples. This multidirectional flow in process 1000 may occur when more pattern recognition algorithms or other machine-learning techniques are utilized. In various embodiments, the computing system may determine how to proceed throughout process 1000 at least in part based on user inputs from an administrative computing system.

At 1045, the computing system may determine whether the artificial intelligence agent has achieved a sufficient proficiency level. The proficiency level may be determined by comparing an accuracy of the artificial intelligence model with one or more predetermined thresholds. The accuracy of the artificial intelligence agent can be tested using a set of test data, which can be a set of data similar to the training data in that it includes ground truth information, but was not used during the training process. If, at 1045, it is determined that the artificial intelligence agent is not sufficiently proficient, process 1000 may continue to 1010 to further train the machine-learning models of the artificial intelligence agent using additional training datasets. On the other hand, if it is determined that the artificial intelligence agent has reached a desired proficiency level, process 1000 may end at 1050, representing the end of the training process.

Figure 11:
FIG. 11 is a block diagram of a generic computing device for realizing methods leading to recursive assessment data collection and predictive healthcare recommendations according to one or more embodiments of the subject matter disclosed herein.

FIG. 11 and the following discussion are intended to provide a brief, general description of a suitable computing environment in which the subject matter disclosed herein may be implemented. Although not required, aspects of the subject matter disclosed herein will be described in the general context of computer-executable instructions, such as program modules, being executed by a personal computer. Generally, program modules include routines, programs, objects, components, data structures, and the like, that perform particular tasks or implement particular abstract data types. Such program module may be embodied in both a transitory and/or a non-transitory computer-readable medium having computer-executable instructions. Moreover, those skilled in the art will appreciate that the invention may be practiced with other computer system configurations, including hand-held devices, cellular or mobile telephones, multiprocessor systems, microprocessor-based or programmable consumer electronics, network PCs, minicomputers, mainframe computers, and the like. The invention may also be practiced in distributed computing environments where tasks are performed by remote processing devices that may be linked through a communications network. In a distributed computing environment, program modules may be located in both local and remote memory storage devices.

FIG. 11 is a diagram illustrating elements or components that may be present in a computer device or system 1100 configured to implement a method, process, function, or operation in accordance with an embodiment of the information disclosed herein. It may include the system, apparatus, methods, processes, functions, and/or operations for enabling efficient configuration and presentation of a user interface to a user, based on the user's previous behavior, and may be wholly or partially implemented in the form of a set of instructions executed by one or more programmed computer processors, such as a central processing unit (CPU) or microprocessor. Such processors may be incorporated in an apparatus, server, client or other computing or data processing device operated by, or in communication with, other components of the system. FIG. 7 illustrates elements or components that may be present in a computer device or system 700 configured to implement a method, process, function, or operation in accordance with an embodiment. The subsystems shown in FIG. 11 are interconnected via a system bus 1102. Additional subsystems include a printer 1104, a keyboard 1106, a fixed disk 1108, and a monitor 1110, which is coupled to a display adapter 1112. Peripherals and input/output (I/O) devices, which couple to an I/O controller 1114, can be connected to the computer system by any number of means known in the art, such as a serial port 1116. For example, the serial port 1116 or an external interface 1118 can be utilized to connect the computer device 1100 to additional devices and/or systems not shown in FIG. 11, including a wide area network (such as the Internet), a mouse input device, and/or a scanner. The interconnection via the system bus 1102 allows one or more processors 1120 to: communicate with each subsystem, control the execution of instructions that may be stored in a system memory 1122 and/or the fixed disk 1108, and to exchange information between subsystems. The system memory 1122 and/or the fixed disk 1108 may represent any tangible computer-readable medium.

The subject matter described herein can be implemented in software in combination with hardware and/or firmware.

For example, the subject matter described herein may be implemented in software executed by one or more processors. In one exemplary implementation, the subject matter described herein may be implemented using a non-transitory computer-readable medium having stored thereon computer executable instructions that when executed by the processor of a computer control the computer to perform steps. Exemplary computer-readable media suitable for implementing the subject matter described herein include non-transitory computer-readable media, such as disk memory devices, chip memory devices, programmable logic devices, and application-specific integrated circuits. In addition, a computer-readable medium that implements the subject matter described herein may be located on a single device or computing platform or may be distributed across multiple devices or computing platforms.

The system may use a bus 1102 that can be any of several types of suitable bus structure(s) including the memory bus or memory controller, a peripheral bus or external bus, and/or a local bus using any suitable variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

The systems and methods herein enable rapid ingestion of big data sets in a distributed computing environment. The metadata-driven approach intake processing reduces source ingestion time, enhances reliability, and automates data intake. Furthermore, the platform agnostic nature of the present disclosure can operate on an input source in any electronic format. The error logging and reporting of the present disclosure further enable users to monitor progress and identify bad data based on predetermined or dynamically generated validation tolerances.

As used herein, "match" or "associated with" or similar phrases may include an identical match, a partial match, meeting certain criteria, matching a subset of data, a correlation, satisfying certain criteria, some correspondence, an association, an algorithmic relationship and/or the like. Similarly, as used herein, "authenticate" or similar terms may include an exact authentication, a partial authentication, authenticating a subset of data, some correspondence, satisfying certain criteria, an association, an algorithmic relationship and/or the like.

Any communication, transmission and/or channel discussed herein may include any system or method for delivering content (e.g., data, information, metadata, and the like), and/or the content itself. The content may be presented in any form or medium, and in various embodiments, the content may be delivered electronically and/or capable of being presented electronically. For example, a channel may comprise a website or device (e.g., Facebook, YOUTUBE®, APPLE®TV®, PANDORA®, XBOX®, SONY® PLAYSTATION®), a uniform resource locator ("URL"), a document (e.g., a MICROSOFT® Word® document, a MICROSOFT® Excel® document, an ADOBE®.pdf document, and the like), an "eBook," an "emagazine," an application or microapplication (as described herein), an SMS or other type of text message, an email, Facebook, Twitter, MMS and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network and/or location-based service. Distribution channels may include at least one of a merchant website, a social media site, affiliate or partner websites, an external vendor, and a mobile device communication. Examples of social media sites include FACEBOOK®, FOURSQUARE®, TWITTER®, MYSPACE®, LINKEDIN®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS® NT®, WINDOWS® 95/98/2000®, WINDOWS® XP®, WINDOWS® Vista®, WINDOWS® 7®, OS2, UNIX®, LINUX®, SOLARIS®, MacOS, and the like) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations. Useful machines for performing the various embodiments include general purpose digital computers or similar devices.

In fact, in various embodiments, the embodiments are directed toward one or more computer systems capable of carrying out the functionality described herein. The computer system includes one or more processors, such as processor. The processor is connected to a communication infrastructure (e.g., a communications bus, cross-over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a display unit.

Computer system also includes a main memory, such as for example random access memory (RAM), and may also include a secondary memory. The secondary memory may include, for example, a hard disk drive and/or a removable storage drive, representing a floppy disk drive, a magnetic tape drive, an optical disk drive, etc. The removable storage drive reads from and/or writes to a removable storage unit in a well-known manner. Removable storage unit represents a floppy disk, magnetic tape, optical disk, etc., which is read by and written to by the removable storage drive. As will be appreciated, the removable storage unit includes a computer-usable storage medium having stored therein computer software and/or data.

In various embodiments, secondary memory may include other similar devices for allowing computer programs or other instructions to be loaded into computer system. Such devices may include, for example, a removable storage unit and an interface. Examples of such may include a program cartridge and cartridge interface (such as that found in video game devices), a removable memory chip (such as an erasable programmable read only memory (EPROM), or programmable read only memory (PROM)) and associated socket, and other removable storage units and interfaces, which allow software and data to be transferred from the removable storage unit to computer system.

Computer system may also include a communications interface. Communications interface allows software and data to be transferred between computer system and external devices. Examples of communications interface may include a modem, a network interface (such as an Ethernet account), a communications port, a Personal Computer Memory Account International Association (PCMCIA) slot and account, etc. Software and data transferred via communications interface are in the form of signals which may be electronic, electromagnetic, optical, or other signals capable of being received by communications interface. These signals are provided to communications interface via a communications path (e.g., channel). This channel carries signals and may be implemented using wire, cable, fiber optics, a telephone line, a cellular 30 link, a radio frequency (RF) link, wireless and other communications channels.

The terms "computer program medium" and "computer-usable medium" and "computer-readable medium" are used to generally refer to media such as removable storage drive and a hard disk installed in hard disk drive. These computer program products provide software to computer system.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into computer system using removable storage drive, hard disk drive or communications interface. The control logic (software), when executed by the processor, causes the processor to perform the functions of various embodiments as described herein. In various embodiments, hardware may include components such as application-specific integrated circuits (ASICs). Implementation of the hardware state machine so as to perform the functions described herein will be apparent to persons skilled in the relevant art(s).

The various system components may be independently, separately or collectively suitably coupled to the network via data links which includes, for example, a connection to an Internet Service Provider (ISP) over the local loop as is typically used in connection with standard modem communication, cable modem, Dish Networks®, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

Any databases discussed herein may include relational, hierarchical, graphical, or object-oriented structure and/or any other database configurations. Common database products that may be used to implement the databases include DB2 by IBM® (Armonk, N.Y.), various database products available from ORACLE® Corporation (Redwood Shores, Calif.), MICROSOFT® Access® or MICROSOFT® SQL Server® by MICROSOFT® Corporation (Redmond, Wash.), MySQL by MySQL AB (Uppsala, Sweden), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

One skilled in the art will also appreciate that, for security reasons, any databases, systems, devices, servers, or other components of the system may consist of any combination thereof at a single location or at multiple locations, wherein each database or system includes any of various suitable security features, such as firewalls, access codes, encryption, decryption, compression, decompression, and/or the like.

The computers discussed herein may provide a suitable website or other Internet-based graphical user interface which is accessible by users. In one embodiment, the MICROSOFT® INTERNET INFORMATION SER-VICES® (IIS), MICROSOFT® Transaction Server (MTS), and MICROSOFT® SQL Server, are used in conjunction with the MICROSOFT® operating system, MICROSOFT® NT web server software, a MICROSOFT® SQL Server database system, and a MICROSOFT® Commerce Server. Additionally, components such as Access or MICROSOFT® SQL Server, ORACLE®, Sybase, Informix, MySQL, Interbase, and the like, may be used to provide an Active Data Object (ADO) compliant database management system. In one embodiment, the Apache web server is used in conjunction with a Linux operating system, a MySQL database, and the Perl, PHP, and/or Python programming languages.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® APPLE®, JAVASCRIPT, active server pages (ASP) common gateway interface scripts (CGI), extensible markup language (XML), dynamic HTML, cascading style sheets (CSS), AJAX (Asynchronous JAVASCRIPT and XML), helper applications, plug-ins, and the like. A server may include a web service that receives a request from a web server, the request including a URL and an IP address (123.56.555.234). The web server retrieves the appropriate web pages and sends the data or applications for the web pages to the IP address. Web services are applications that are capable of interacting with other applications over a communication means, such as the internet. Web services are typically based on standards or protocols such as XML, SOAP, AJAX, WSDL and UDDI. Web services methods are well known in the art and are covered in many standard texts. See, e.g., ALEX NGHIEM, IT WEB SERVICES: A ROADMAP FOR THE ENTERPRISE (2003), hereby incorporated by reference.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on an Internet server. Middleware may be configured to process transactions between the various components of an application server and any number of internal or external systems for any of the purposes disclosed herein. WEBSPHERE MQ™ (formerly MQSeries) by IBM®, Inc. (Armonk, N.Y.) is an example of a commercially available middleware product. An Enterprise Service Bus ("ESB") application is another example of middleware.

Practitioners will also appreciate that there are a number of methods for displaying data within a browser-based document. Data may be represented as standard text or within a fixed list, scrollable list, drop-down list, editable text field, fixed text field, pop-up window, maps, color-coded data sets, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as R, C, C++, C #, JAVA®, JAVASCRIPT, VBScript, Macromedia Cold Fusion, COBOL, MICROSOFT® Active Server Pages, assembly, PERL, PHP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "JAVA® Cryptography" by Jonathan Knudson, published by O'Reilly & Associates (1998); (3) "Cryptography & Network Security: Principles & Practice" by William Stallings, published by Prentice Hall; all of which are hereby incorporated by reference.

As will be appreciated by one of ordinary skill in the art, the system may be embodied as a customization of an existing system, an add-on product, a processing apparatus executing upgraded software, a standalone system, a distributed system, a method, a data processing system, a device for data processing, and/or a computer program product. Accordingly, any portion of the system or a module may take the form of a processing apparatus executing code, an Internet-based embodiment, an entirely hardware embodiment, or an embodiment combining aspects of the Internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method are described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general-purpose computer, special-purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special-purpose hardware-based computer systems which perform the specified functions or steps, or suitable combinations of special-purpose hardware and computer instructions. Further, illustrations of process flow and the descriptions thereof may make reference to use WINDOWS®, webpages, websites, web forms, prompts, and the like. Practitioners will appreciate that the illustrated steps described herein may comprise in any number of configurations including the use of WINDOWS®, webpages, web forms, popup WINDOWS®, prompts and the like. It should be further appreciated that the multiple steps as illustrated and described may be combined into single webpages and/or WINDOWS® but have been expanded for the sake of simplicity. In other cases, steps illustrated and described as single process steps may be separated into multiple webpages and/or WINDOWS® but have been combined for simplicity.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Systems, methods, and computer program products are provided. In the detailed description herein, references to "various embodiments", "one embodiment", "an embodiment", "an example embodiment", and the like, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. References to "or" may be construed as inclusive so that any terms described using "or" may indicate any of a single, more than one, and all of the described terms.

Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims.

Furthermore, no element, component, or method step in the present disclosure is intended to be dedicated to the public regardless of whether the element, component, or method step is explicitly recited in the claims. No claim element herein is to be construed under the provisions of 35 U.S.C. 112 (f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has" or "having" are used in either the detailed description or the claims, such terms are intended to be inclusive in a manner similar to the term "comprising" as "comprising" is interpreted when employed as a transitional word in a claim.

Since many modifications, variations, and changes in detail can be made to the described preferred embodiments of the subject matter, it is intended that all matters in the foregoing description and shown in the accompanying drawings be interpreted as illustrative and not in a limiting sense. Thus, the scope of the subject matter should be determined by the appended claims and their legal equivalence.

What is claimed is:

1. A method comprising:

providing an artificial intelligence (AI) agent to a patient to assess the patient via a user interface presented on a computing device, wherein the user interface dynamically alters a sequence of assessment questions presented to the patient based on at least one answer received from the patient, wherein the AI agent was trained by:

generating, based on session logs of a cohort of subjects interacting with the user interface, one or more training datasets comprising (i) data on user interactions with the user interface by subjects in the cohort, and (ii) data based on health records of the subjects in the cohort of subjects;

the AI agent by:

processing the one or more training datasets to extract one or more features indicative of user interaction patterns and health characteristics, inputting the one or more features into the AI agent, iteratively training the AI agent by adjusting one or more trainable parameters of the AI agent to reduce an error between predicted and actual healthcare recommendations indicated in the health records, and validating the AI agent using a portion of the one or more training datasets until a predetermined proficiency or accuracy threshold is satisfied, wherein training the AI agent comprises applying a regression model to identify causal factors for one or more medical screenings or procedures based on interactions of the subjects with the user interface;

generating, based on interactions of the patient with the AI agent and on data in an electronic health record of the patient, a recommendation for at least one of a medical screening or a medical procedure; and presenting the recommendation to at least one of the patient or a healthcare provider of the patient.

2. The method of claim 1, further comprising administering the recommended medical screening or the recommended medical procedure to the patient.

3. The method of claim 1, further comprising updating the AI agent based on the interactions of the patient with the AI agent.

4. The method of claim 3, wherein updating the AI agent comprises generating one or more updated training datasets and applying one or more machine-learning techniques to the updated training datasets.

5. The method of claim 1, wherein training the AI agent further comprises applying a pattern recognition model or a classification model to recognize normal or abnormal patterns of interaction with the user interface.

6. The method of claim 1, wherein training the AI agent further comprises applying a decisioning model to identify interactions suited to obtaining certain information on subjects through the user interface.

7. The method of claim 1, wherein training the AI further comprises applying natural language processing (NLP) to responses by the subjects in the cohort.

8. The method of claim 1, wherein the user interface digitally presents a plurality of assessment questions to the patient using an interactive display on a computing device, wherein at least one assessment question comprises an assessment question suited to having multiple simultaneous answers.

9. The method of claim 6, wherein the AI agent, in response to receiving one answer to an assessment question suited to having multiple simultaneous answers, updates assessment data about the patient in an assessment database and recursively presents the assessment question suited to having multiple simultaneous answers to the patient again.

10. The method of claim 9, wherein the AI agent iteratively analyzes answers stored in the assessment database after each update to determine whether the stored answers indicate that the recommendation should be triggered.

11. The method of claim 10, wherein presenting the recommendation comprises electronically communicating assessment data and the recommendation to the healthcare provider.

12. The method of claim 1, wherein the data on user interactions indicates selections made through the user interface.

13. The method of claim 1, wherein the data on user interactions includes text entries submitted through the user interface.

14. The method of claim 1, wherein the data based on health records identifies at least one of medical screenings administered to the subjects in the cohort, medical procedures administered to subjects the subjects in the cohort, or medical conditions of the subjects in the cohort.

15. A computing system comprising one or more processors configured to:

provide an artificial intelligence (AI) agent to a patient to assess the patient via a user interface presented on a computing device, wherein the user interface dynamically alters a sequence of assessment questions presented to the patient based on at least one answer received from the patient, wherein the AI agent was trained by:

generating, based on session logs of a cohort of subjects interacting with the user interface, one or more training datasets comprising (i) data on user interactions with the user interface by subjects in the cohort, and (ii) data based on health records of the subjects in the cohort of subjects;

training the AI agent by:

processing the one or more training datasets to extract one or more features indicative of user interaction patterns and health characteristics, inputting the one or more features into the AI agent, iteratively training the AI agent by adjusting one or more trainable parameters of the AI agent to reduce an error between predicted and actual healthcare recommendations indicated in the health records, and validating the AI agent using a portion of the one or more training datasets until a predetermined proficiency or accuracy threshold is satisfied, wherein training the AI agent comprises applying a regression model to identify causal factors for one or more medical screenings or procedures based on interactions of the subjects with the user interface;

generate, based on interactions of the patient with the AI agent and on data in an electronic health record of the patient, a recommendation for at least one of a medical screening or a medical procedure; and present the recommendation to at least one of the patient or a healthcare provider of the patient.

16. The computing system of claim 15, wherein training the AI agent further comprises at least one of applying:

a pattern recognition model or a classification model to recognize normal or abnormal patterns of interaction with the user interface;

a decisioning model to identify interactions suited to obtaining certain information on subjects through the user interface; or natural language processing (NLP) to responses submitted by the subjects in the cohort.

17. The computing system of claim 15, wherein:

the user interface digitally presents a plurality of assessment questions to the patient using an interactive display on the computing device, wherein at least one assessment question comprises an assessment question suited to having multiple simultaneous answers;

the AI agent, in response to receiving one answer to an assessment question suited to having multiple simultaneous answers, updates assessment data about the patient in an assessment database and recursively presents the assessment question suited to having multiple simultaneous answers to the patient again; and the AI agent iteratively analyzes answers stored in the assessment database after each update to determine whether the stored answers indicate that the recommendation should be triggered.

18. The computing system of claim 15, wherein:

the data on user interactions includes selections made through the user interface and text entries submitted through the user interface; and the data based on health records identifies at least one of medical screenings administered to the subjects in the cohort, medical procedures administered to the subjects in the cohort, or medical conditions of the subjects in the cohort.

19. The method of claim 1, wherein altering the user interface comprises re-presenting at least one assessment question configured to accept multiple simultaneous answers to solicit additional different answers from the patient.

20. The computing system of claim 15, wherein altering the user interface comprises re-presenting at least one assessment question configured to accept multiple simultaneous answers to solicit additional different answers from the patient.

* * * * *